US012661110B2

(12) United States Patent
Sugimoto et al.

(10) Patent No.: US 12,661,110 B2
(45) Date of Patent: Jun. 23, 2026

(54) MEDICAL STAPLER

(71) Applicants: OLYMPUS CORPORATION, Tokyo
(JP); National Cancer Center, Tokyo
(JP)

(72) Inventors: Arimasa Sugimoto, Hachioji (JP);
Satoru Nonaka, Tokyo (JP)

(73) Assignees: National Cancer Center, Tokyo (JP);
OLYMPUS CORPORATION, Tokyo
(JP)

( * ) Notice: Subject to any disclaimer, the term of this
patent is extended or adjusted under 35
U.S.C. 154(b) by 0 days.

(21) Appl. No.: 19/037,336

(22) Filed: Jan. 27, 2025

(65) Prior Publication Data

US 2025/0241640 A1     Jul. 31, 2025

Related U.S. Application Data

(63) Continuation of application No.
PCT/JP2024/002678, filed on Jan. 29, 2024.

(51) Int. Cl.
A61B 17/068          (2006.01)
A61B 1/00            (2006.01)
              (Continued)

(52) U.S. Cl.
CPC ........ A61B 17/0682 (2013.01); A61B 1/0008
(2013.01); A61B 1/00128 (2013.01);
              (Continued)

(58) Field of Classification Search
CPC .............. A61B 17/0682; A61B 1/0008; A61B
1/00128; A61B 17/00234; A61B 90/39;
              (Continued)

(56) References Cited

U.S. PATENT DOCUMENTS 4,523,707 A * 6/1985 Blake, III .......... A61B 17/0684
227/19
4,773,420 A * 9/1988 Green .................... A61B 17/11
227/19
(Continued)

FOREIGN PATENT DOCUMENTS

EP        1929963 A1 *  6/2008   ........... A61B 17/072
EP        3167818 B1 *  8/2019   ........... A61B 17/068
(Continued)

OTHER PUBLICATIONS

"International Application No. PCT/JP2024/002678, International
Search Report dated Apr. 9, 2024", w/ English Translation, (Apr. 9,
2024), 4 pgs.

*Primary Examiner* — Robert F Long
(74) *Attorney, Agent, or Firm* — Schwegman Lundberg &
Woessner, P.A.

(57)          ABSTRACT

A medical stapler provided at a distal end of an endoscope
includes a wire extending in an axial direction of the
endoscope and a staple release part having a cartridge
configured to accommodate a staple and an injection mecha-
nism connected to a distal end of the wire and configured to
eject the staple from the cartridge. The cartridge is provided
so that the cartridge is removably attached to the staple
release part. The injection mechanism is movable from a
first position that is an initial position to a second position
where the staple is ejected by manipulating the wire. The
injection mechanism is located at the second position when
the cartridge is removed from the staple release part. The
injection mechanism moves from the second position to the
first position when the cartridge is attached to the staple
release part.

15 Claims, 21 Drawing Sheets

(51) Int. Cl.

| A61B 17/00 | (2006.01) |
|---|---|
| A61B 90/00 | (2016.01) |

(52) U.S. Cl.

CPC ........ A61B 17/00234 (2013.01); A61B 90/39
(2016.02); *A61B 2017/00296* (2013.01); *A61B*
*2017/00477* (2013.01); *A61B 2090/3937*
(2016.02)

(58) Field of Classification Search

CPC ........... A61B 2017/00296; A61B 2017/00477;
A61B 2090/3937; A61B 1/00087; A61B
1/00133; A61B 1/0014
USPC ......... 227/175.1–182.1, 8, 19; 606/139, 142,
606/143, 205–208
See application file for complete search history.

(56) References Cited

U.S. PATENT DOCUMENTS

| | | | | |
|---|---|---|---|---|
| 5,158,567 A | * | 10/1992 | Green | A61B 17/072 |
| | | | | 411/457 |
| 5,356,064 A | * | 10/1994 | Green | A61B 17/0684 |
| | | | | 606/139 |
| 5,403,326 A | * | 4/1995 | Harrison | A61B 17/10 |
| | | | | 227/181.1 |
| 5,433,721 A | * | 7/1995 | Hooven | A61B 17/068 |
| | | | | 606/139 |
| 5,452,836 A | * | 9/1995 | Huitema | A61B 17/072 |
| | | | | 227/176.1 |
| 5,465,894 A | * | 11/1995 | Clark | A61B 17/072 |
| | | | | 227/19 |
| 5,470,010 A | * | 11/1995 | Rothfuss | A61B 17/105 |
| | | | | 227/19 |
| 5,484,095 A | * | 1/1996 | Green | A61B 17/0686 |
| | | | | 227/181.1 |
| 5,680,981 A | * | 10/1997 | Mililli | A61B 17/0684 |
| | | | | 227/176.1 |
| 6,302,311 B1 | * | 10/2001 | Adams | A61B 17/115 |
| | | | | 227/176.1 |
| 6,601,749 B2 | * | 8/2003 | Sullivan | A61B 17/07207 |
| | | | | 227/176.1 |
| 6,808,491 B2 | * | 10/2004 | Kortenbach | A61B 10/06 |
| | | | | 600/153 |
| 7,056,330 B2 | * | 6/2006 | Gayton | A61B 17/0684 |
| | | | | 606/139 |
| 7,087,010 B2 | * | 8/2006 | Ootawara | A61B 1/00098 |
| | | | | 600/129 |
| 7,736,374 B2 | * | 6/2010 | Vaughan | A61B 17/0401 |
| | | | | 606/205 |
| 7,744,613 B2 | * | 6/2010 | Ewers | A61B 17/0487 |
| | | | | 606/232 |
| 7,776,057 B2 | * | 8/2010 | Laufer | A61B 17/0401 |
| | | | | 606/139 |
| 7,914,543 B2 | * | 3/2011 | Roth | A61F 5/0083 |
| | | | | 227/175.1 |
| 8,863,748 B2 | * | 10/2014 | Kuroda | A61B 17/0401 |
| | | | | 600/106 |
| 11,771,422 B2 | * | 10/2023 | Fernandes | A61B 17/0686 |
| | | | | 227/175.1 |
| 11,998,187 B2 | * | 6/2024 | Karasawa | A61B 17/0469 |
| 2003/0199924 A1 | * | 10/2003 | Coleman | A61B 17/0644 |
| | | | | 606/213 |
| 2004/0138682 A1 | * | 7/2004 | Onuki | A61B 17/0643 |
| | | | | 606/205 |
| 2007/0043384 A1 | * | 2/2007 | Ortiz | A61B 17/0401 |
| | | | | 606/142 |
| 2007/0114261 A1 | * | 5/2007 | Ortiz | A61B 17/07207 |
| | | | | 227/175.1 |
| 2007/0162056 A1 | * | 7/2007 | Gerbi | A61B 17/29 |
| | | | | 606/153 |
| 2007/0213585 A1 | * | 9/2007 | Monassevitch | A61B 17/0643 |
| | | | | 600/104 |

| | | | | |
|---|---|---|---|---|
| 2007/0282356 A1 | * | 12/2007 | Sonnenschein | A61B 17/068 |
| | | | | 606/153 |
| 2008/0000941 A1 | * | 1/2008 | Sonnenschein | A61B 17/07207 |
| | | | | 227/120 |
| 2008/0173691 A1 | * | 7/2008 | Mas | A61B 17/0057 |
| | | | | 227/175.1 |
| 2008/0210738 A1 | * | 9/2008 | Shelton | A61B 17/0643 |
| | | | | 227/176.1 |
| 2008/0217376 A1 | * | 9/2008 | Clauson | A61B 17/0684 |
| | | | | 227/181.1 |
| 2008/0249565 A1 | * | 10/2008 | Michler | A61B 17/10 |
| | | | | 227/175.1 |
| 2008/0296344 A1 | * | 12/2008 | Cropper | A61B 17/0684 |
| | | | | 227/176.1 |
| 2009/0039137 A1 | * | 2/2009 | Viola | A61B 17/07207 |
| | | | | 227/176.1 |
| 2009/0069806 A1 | * | 3/2009 | De La Mora Levy | |
| | | | | A61B 17/072 |
| | | | | 606/198 |
| 2009/0206137 A1 | * | 8/2009 | Hall | A61B 17/07207 |
| | | | | 227/176.1 |
| 2009/0242609 A1 | * | 10/2009 | Kanner | A61B 17/0057 |
| | | | | 227/175.1 |
| 2010/0213240 A1 | * | 8/2010 | Kostrzewski | A61B 17/3209 |
| | | | | 227/180.1 |
| 2010/0320252 A1 | * | 12/2010 | Viola | A61B 17/068 |
| | | | | 227/176.1 |
| 2010/0327042 A1 | * | 12/2010 | Amid | A61B 17/0684 |
| | | | | 227/176.1 |
| 2011/0248064 A1 | * | 10/2011 | Marczyk | A61B 17/07207 |
| | | | | 227/114 |
| 2012/0273548 A1 | * | 11/2012 | Ma | A61B 5/7282 |
| | | | | 227/176.1 |
| 2013/0306704 A1 | * | 11/2013 | Balbierz | A61F 5/0086 |
| | | | | 227/176.1 |
| 2014/0021240 A1 | * | 1/2014 | Miyamoto | A61B 17/07207 |
| | | | | 227/176.1 |
| 2016/0058439 A1 | * | 3/2016 | Shelton, IV | A61B 17/105 |
| | | | | 227/176.1 |
| 2016/0303743 A1 | * | 10/2016 | Rockrohr | A61B 34/30 |
| 2017/0020524 A1 | * | 1/2017 | Marczyk | A61B 17/105 |
| 2017/0189026 A1 | * | 7/2017 | Felder | A61B 17/11 |
| 2017/0196554 A1 | * | 7/2017 | Rousseau | A61B 17/068 |
| 2017/0281177 A1 | * | 10/2017 | Harris | A61B 17/0686 |
| 2018/0199941 A1 | * | 7/2018 | Thompson | A61B 17/3468 |
| 2019/0167267 A1 | * | 6/2019 | Kobayashi | A61B 17/07207 |
| 2019/0200982 A1 | * | 7/2019 | Kumada | A61B 17/0684 |
| 2020/0078007 A1 | * | 3/2020 | O'Hara | A61B 17/06128 |
| 2020/0275925 A1 | * | 9/2020 | Smith | A61B 1/018 |
| 2020/0337700 A1 | * | 10/2020 | Hontz | A61B 17/072 |
| 2021/0293002 A1 | * | 9/2021 | Bierwith | E02F 9/2841 |
| 2022/0280158 A1 | * | 9/2022 | Estevez | A61B 1/00087 |
| 2022/0354607 A1 | * | 11/2022 | Rector | A61B 90/98 |
| 2023/0000495 A1 | * | 1/2023 | Barrera | A61B 17/28 |
| 2023/0082982 A1 | * | 3/2023 | Karasawa | A61B 17/0469 |
| | | | | 606/139 |
| 2023/0193698 A1 | * | 6/2023 | Dreier | E21B 17/03 |
| | | | | 175/320 |
| 2023/0218336 A1 | * | 7/2023 | Higuchi | A61B 90/39 |
| | | | | 606/46 |
| 2023/0329684 A1 | * | 10/2023 | Nakamura | A61B 17/00 |
| 2023/0329705 A1 | * | 10/2023 | Nakamura | A61B 1/00101 |
| 2023/0329706 A1 | * | 10/2023 | Nakamura | A61B 1/00101 |
| 2023/0329708 A1 | * | 10/2023 | Nakamura | A61B 1/00135 |
| 2024/0081796 A1 | * | 3/2024 | Sugimoto | A61B 17/0469 |
| 2024/0197302 A1 | * | 6/2024 | Nakamura | A61B 1/00087 |
| 2025/0082327 A1 | * | 3/2025 | Ueda | A61B 1/2676 |
| 2025/0160825 A1 | * | 5/2025 | Witte | A61B 17/072 |
| 2025/0169841 A1 | * | 5/2025 | Sugimoto | A61B 17/29 |
| 2025/0228559 A1 | * | 7/2025 | Ding | A61B 17/072 |
| 2025/0241640 A1 | * | 7/2025 | Sugimoto | A61B 17/0682 |

FOREIGN PATENT DOCUMENTS

| | | |
|---|---|---|
| JP | 2008212674 A | 9/2008 |
| JP | 2021500993 A | 1/2021 |
| JP | 2022522470 A | 4/2022 |

(56)          References Cited

FOREIGN PATENT DOCUMENTS

| WO | WO-2013073523 A1 * | 5/2013 | ....... A61B 17/07207 |
| WO | WO-2017199392 A1 * | 11/2017 | .......... A61B 17/068 |
| WO | WO-2019089358 A1 | 5/2019 | |
| WO | WO-2020180678 A1 | 9/2020 | |
| WO | WO-2023248361 A1 | 12/2023 | |

* cited by examiner

FIG. 14

MEDICAL STAPLER

BACKGROUND OF THE INVENTION

Field of the Invention

The present invention relates to a medical stapler. This application is a continuation application based on International Patent Application No. PCT/JP2024/002678 filed on Jan. 29, 2024, and the content of the PCT international application is incorporated herein by reference.

Description of Related Art

In recent years, in an operation of enabling suturing in a lumen, flexible staplers in which a suturing mechanism is supported by a flexible endoscope have been used. When the flexible stapler is used, a needle (hereinafter referred to as a staple) is loaded into the suturing mechanism and inserted into the lumen and an affected area is sutured by ejecting the staple with access to the affected area.

When a plurality of staples are ejected for suturing treatment, it is necessary to perform a process of loading staples a plurality of times. Therefore, it is necessary to perform a manipulation for pulling the staples out of a body once after the staples are ejected and inserting the staples into the body after the staple loading process a plurality of times.

Moreover, in order to reload the staples and eject the staples again, it is necessary to return the suturing mechanism to an initial position. As a method of returning the suturing mechanism to the initial position, a method in which a manipulator performs a manipulation to return to the initial position and a method using a mechanism that automatically returns to the initial position are conceivable.

As a conventional medical stapler, for example, there is a surgical stapling device described in Patent Document 1. The surgical stapling device described in Patent Document 1 includes a firing trigger manipulated by a doctor (a manipulator) when a staple is fired, and a spring for returning the firing trigger to an initial position after the staple is fired.

Patent Document 1: Japanese Unexamined Patent Application, First Publication No. 2008-212674

SUMMARY OF THE INVENTION

However, when the mechanism that automatically returns to the initial position such as the surgical stapling device described in Patent Document 1 is used, there is a concern that the number of constituent parts will increase due to the complexity of the mechanism and the size of the parts will increase. Moreover, it may be difficult for the manipulator to recognize whether or not the mechanism has been automatically returned to the initial position. On the other hand, when the manipulator performs a manipulation to return to the initial position, there is a concern that the number of manipulation steps will increase or that the manipulator will not return the mechanism to the initial position due to a forgotten manipulation.

Based on the above circumstances, an objective of the present invention is to provide a medical stapler capable of easily returning a suturing mechanism to an initial position and allowing a manipulator to easily recognize that the suturing mechanism has been returned to the initial position.

In order to solve the above-described problems, the present invention proposes the following means.

According to the present invention, there is provided a medical stapler provided at a distal end of an endoscope, the medical stapler including: a wire extending in an axial direction of the endoscope; and a staple release part having a cartridge configured to accommodate a staple and an injection mechanism connected to a distal end of the wire and configured to eject the staple from the cartridge, wherein the cartridge is provided so that the cartridge is removably attached to the staple release part, wherein the injection mechanism is movable from a first position that is an initial position to a second position where the staple is ejected according to advance and retraction of the wire, wherein the injection mechanism is located at the second position when the cartridge is removed from the staple release part, and wherein the injection mechanism moves from the second position to the first position when the cartridge is attached to the staple release part.

According to the present invention, it is possible to provide a medical stapler capable of easily returning a suturing mechanism to an initial position and allowing a manipulator to easily recognize that the suturing mechanism has been returned to the initial position.

BRIEF DESCRIPTION OF THE DRAWINGS

FIG. 14 is a cross-sectional view of the cap and the grasping part that has advanced.

DETAILED DESCRIPTION OF THE INVENTION

Figure 1:
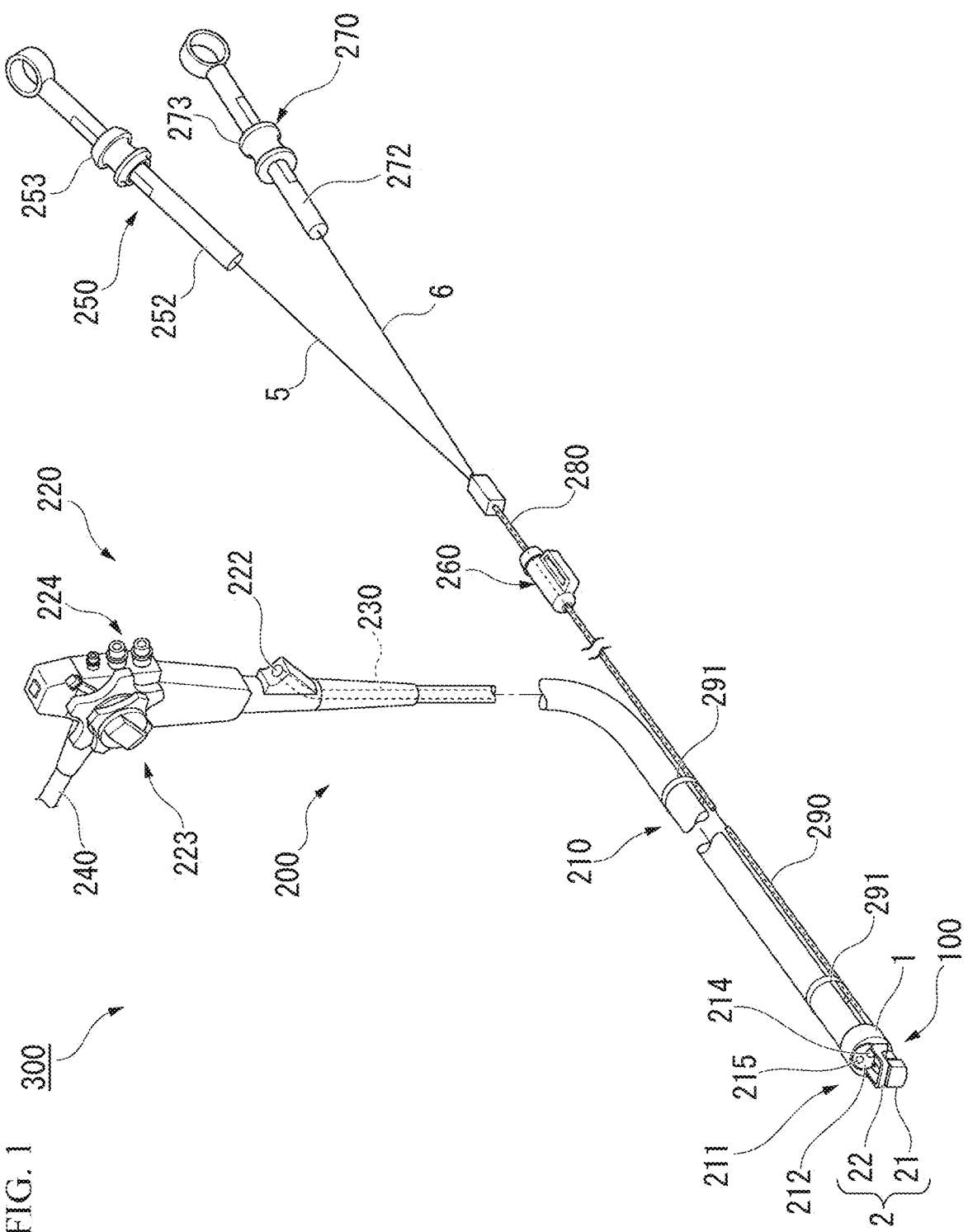
FIG. 1 is a view showing an overall configuration of a medical system including a medical stapler according to the present invention.

A medical stapler 100 according to the present embodiment will be described with reference to the drawings. FIG. 1 is a diagram showing an overall configuration of a medical system 300 including the medical stapler 100.

The medical system 300 is used for an operation of suturing a gastrointestinal tract or the like.

The medical system 300 includes a medical stapler 100, an endoscope 200, an opening/closing manipulation part 250, a release manipulation part 270, a wire sheath 280, a resin sheath (a long part) 290, and a wire sheath manipulation part 260.

The opening/closing manipulation part 250 is a manipulation part that actuates the medical stapler 100 with the opening/closing manipulation wire 5.

The release manipulation part 270 is a manipulation part that actuates the medical stapler 100 with a release manipulation wire (a wire) 6.

[Endoscope 200]

The endoscope 200 is a known flexible endoscope, and includes a long insertion part 210 inserted into a body from its distal end, a manipulation part 220 provided at a proximal end of the insertion part 210, and a universal cord 240.

In the insertion part 210, a treatment tool channel 230 through which an endoscopic treatment tool is inserted is formed. A forceps mouth 214 that is a distal end opening of the treatment tool channel 230 is provided at a distal end 212 of the insertion part 210. The treatment tool channel 230 extends from the distal end 212 of the insertion part 210 to the manipulation part 220.

The distal end part 211 of the insertion part 210 includes an imaging unit (not shown) having a charge-coupled device (CCD) or the like. An objective lens 215 of the imaging unit is exposed at the distal end 212 of the insertion part 210. The distal end part 211 of the insertion part 210 has a hard part 211a (see FIG. 14) on a distal end side.

A knob 223 for manipulating the insertion part 210, a switch 224 for manipulating the imaging unit, and the like are provided on a proximal end side of the manipulation part 220. The practitioner (the manipulator) can bend the insertion part 210 in a desired direction by manipulating the knob 223.

A forceps insertion port 222 that communicates with the treatment tool channel 230 is provided on the distal end side of the manipulation part 220. The practitioner can insert an endoscopic treatment tool into the treatment tool channel 230 from the forceps insertion port 222.

The universal cord 240 connects the manipulation part 220 and an external peripheral device. The universal cord 240 outputs, for example, an image captured by the imaging unit to an external device. The image captured by the imaging unit is displayed on a display device such as a liquid crystal display via an image processing device.

[Opening/Closing Manipulation Part 250]

The opening/closing manipulation part 250 is a manipulation part that opens and closes the medical stapler 100 by manipulating the opening/closing manipulation wire 5. As shown in FIG. 1, the opening/closing manipulation part 250 includes an opening/closing manipulation part body 252 and an opening/closing manipulation slider 253.

The proximal end of the opening/closing manipulation wire 5 is connected to the opening/closing manipulation slider 253. The practitioner can advance and retract the opening/closing manipulation wire 5 by advancing and retracting the opening/closing manipulation slider 253 in a longitudinal axis direction with respect to the opening/closing manipulation part body 252.

[Release Manipulation Part 270]

The release manipulation part 270 is a manipulation part that releases a staple S (see FIG. 12) from the medical stapler 100 by manipulating the release manipulation wire 6. As shown in FIG. 1, the release manipulation part 270 includes a release manipulation part body 272 and a release manipulation slider 273.

The proximal end of the release manipulation wire 6 is connected to the release manipulation slider 273. The practitioner can advance and retract the release manipulation wire 6 by advancing and retracting the release manipulation slider 273 in the longitudinal axis direction with respect to the release manipulation part body 272.

[Wire Sheath 280]

The wire sheath 280 is a sheath through which the opening/closing manipulation wire 5 and the release manipulation wire 6 are inserted. The wire sheath 280 is a metallic coil sheath. In addition, the wire sheath 280 is not limited to the metallic coil sheath and may be a sheath of another aspect.

Two inner sheaths 282 (see FIG. 14) are inserted into the wire sheath 280. The opening/closing manipulation wire 5 and the release manipulation wire 6 are inserted into the two inner sheaths 282 respectively. In addition, the two inner sheaths 282 may be multi-lumen tubes having two lumens.

[Resin Sheath 290]

The resin sheath 290 is a sheath through which the wire sheath 280 can be inserted so that the wire sheath 280 can advance and retract. The resin sheath 290 is formed of a resin material. As shown in FIG. 1, the distal end side of the resin sheath 290 is connected to the insertion part 210 of the endoscope 200 by a band 291. The distal end of the resin sheath 290 is fixed to a cap 1 of the medical stapler 100. Moreover, the proximal end of the resin sheath 290 is fixed to the wire sheath manipulation part 260.

[Wire Sheath Manipulation Part 260]

Figure 2:
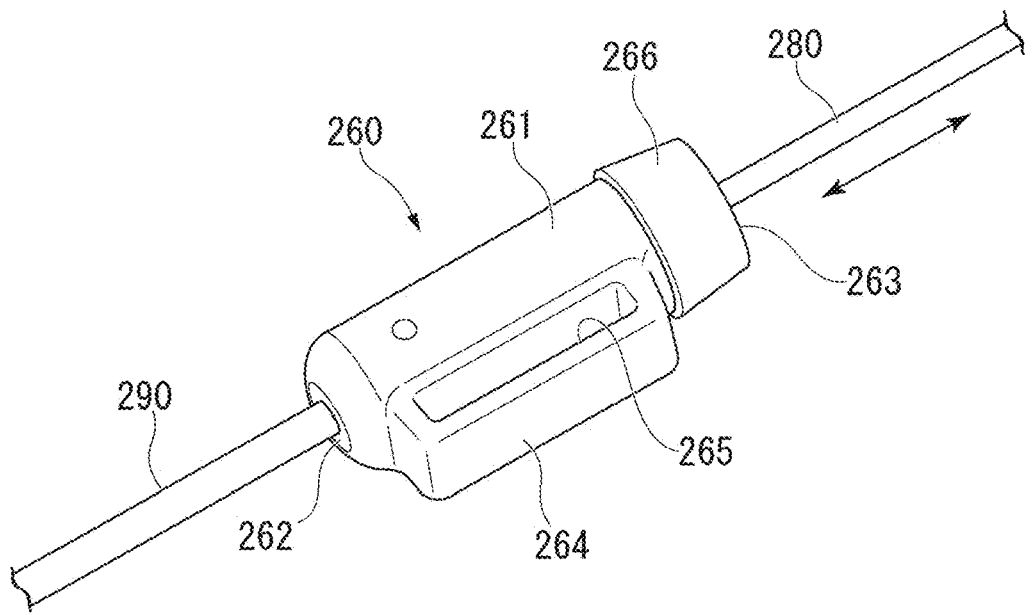
FIG. 2 is a perspective view of a wire sheath manipulation part provided in the medical stapler.

FIG. 2 is a perspective view of the wire sheath manipulation part 260.

The wire sheath manipulation part 260 is a manipulation part that advances and retracts the wire sheath 280 with respect to the resin sheath 290. The wire sheath manipulation part 260 includes a manipulation part body 261 and a band mounting part 264.

The manipulation part body 261 is formed in a cylindrical shape and has a distal end opening 262 and a proximal end opening 263. The proximal end of the resin sheath 290 is fixed to the distal end opening 262.

The wire sheath 280 extends from the proximal end opening 263. The practitioner can advance and retract the wire sheath 280 with respect to the resin sheath 290 by advancing and retracting the wire sheath 280 with respect to the manipulation part body 261.

The band mounting part 264 is a member attached to the manipulation part body 261 and has a band insertion hole 265. By attaching a band (not shown) through which the band insertion hole 265 has passed to the endoscope 200, the manipulation part body 261 can be easily fixed to the endoscope 200.

By fixing the manipulation part body 261 to the endoscope 200, the practitioner can advance and retract the wire sheath 280 with respect to the resin sheath 290 without holding the manipulation part body 261 by hand.

A rubber stopper 266 in contact with the wire sheath 280 is provided in the proximal end opening 263 where the wire sheath 280 extends. A friction force generated between the wire sheath 280 and the rubber stopper 266 can suppress the unintentional advance and retraction operation of the wire sheath 280 in the treatment.

[Medical Stapler 100]

Figure 3:
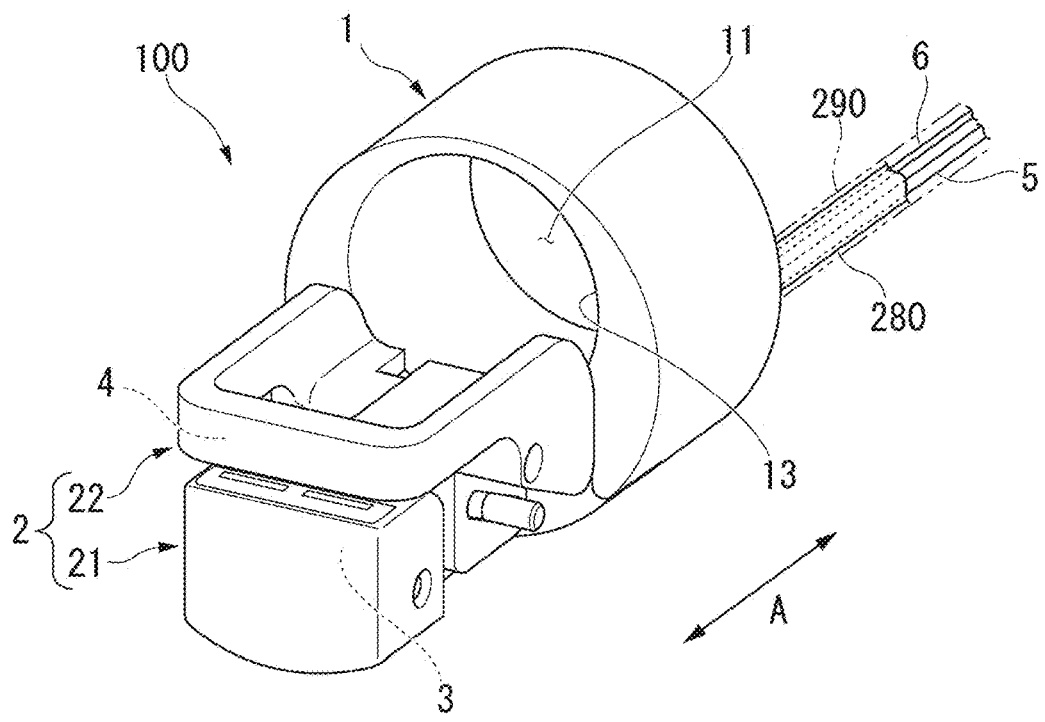
FIG. 3 is a perspective view of the medical stapler.

FIG. 3 is a perspective view of the medical stapler 100. The medical stapler 100 is a suturing mechanism that performs suturing treatment.

The medical stapler 100 includes the cap 1, a grasping part (a suturing part) 2, a staple release part 3, a staple accommodation part 4, an opening/closing manipulation wire 5, and a release manipulation wire 6. The medical stapler 100 is removably attached to the distal end part 211 of the insertion part 210.

Figure 4:
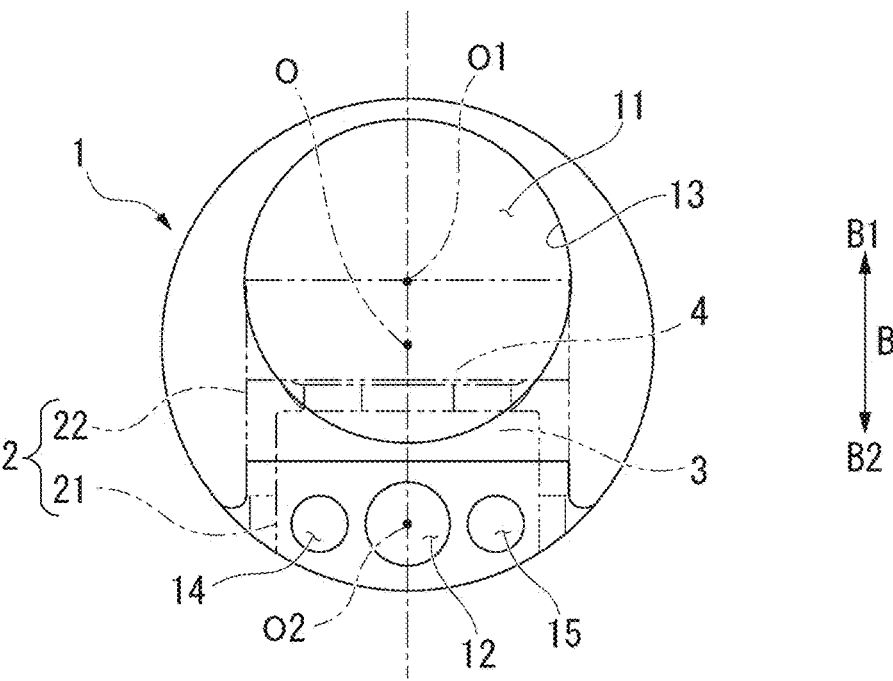
FIG. 4 is a front view of a cap provided in the medical stapler.

FIG. 4 is a front view of the cap 1. In FIG. 4, the grasping part 2 is transparently indicated.

The cap (a detachable part) 1 is a member capable of being removably attached to the distal end part 211 of the endoscope 200. The cap 1 is formed in a substantially cylindrical shape, and has a first through hole 11 penetrating in an axial direction A, a second through hole 12 penetrating in the axial direction A, a third through hole 14 penetrating in the axial direction A, and a fourth through hole 15 penetrating in the axial direction A.

The first through hole 11 is a hole into which the distal end part 211 of the insertion part 210 is inserted. A shape of the first through hole 11 is formed along an external shape of the distal end part 211 of the insertion part 210. Therefore, the distal end part 211 of the endoscope 200 is inserted into the first through hole 11, and therefore the cap 1 can be attached to the distal end part 211 of the endoscope 200.

As shown in FIG. 4, a central axis O1 of the first through hole 11 in the axial direction A is eccentric with respect to a central axis O of the cap 1 in the axial direction A. Here, a direction in which the central axis O1 is eccentric with respect to the central axis O is defined as an "upward direction B1" in a "vertical direction B."

The second through hole 12 is a hole into which the resin sheath 290 is inserted. An inner diameter of the second through hole 12 is substantially the same as an outer diameter of the resin sheath 290. A distal end part of the resin sheath 290 is inserted through the second through hole 12 and fixed.

The wire sheath 280, the opening/closing manipulation wire 5, and the release manipulation wire 6 inserted through the resin sheath 290 are inserted through the second through hole 12 and extended to the distal end side.

As shown in FIG. 4, a central axis O2 of the second through hole 12 in the axial direction A is eccentric with respect to the central axis O of the cap 1 in the axial direction A. A direction in which the central axis O2 is eccentric with respect to the central axis O is opposite to a direction in which the central axis O1 is eccentric with respect to the central axis O (the upward direction B1). A direction in which the central axis O2 is eccentric with respect to the central axis O is a "downward direction B2" in the vertical direction B. In the present embodiment, the upward direction B1 and the downward direction B2 are oriented in the vertical direction B.

The third through hole 14 and the fourth through hole 15 are formed on both sides in a state in which the second through hole 12 is sandwiched therebetween in the front view as seen in a direction along the axial direction A.

Figure 5:
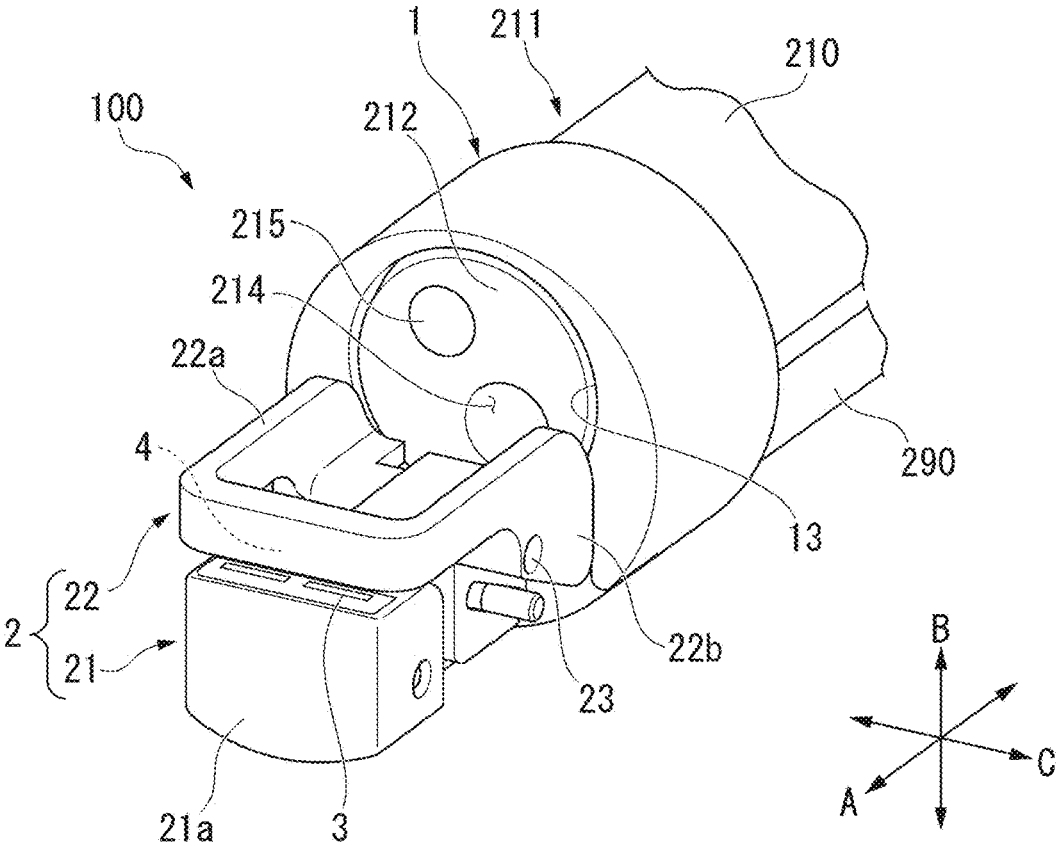
FIG. 5 is a perspective view of the medical stapler in which a grasping part is in a closed state.
Figure 6:
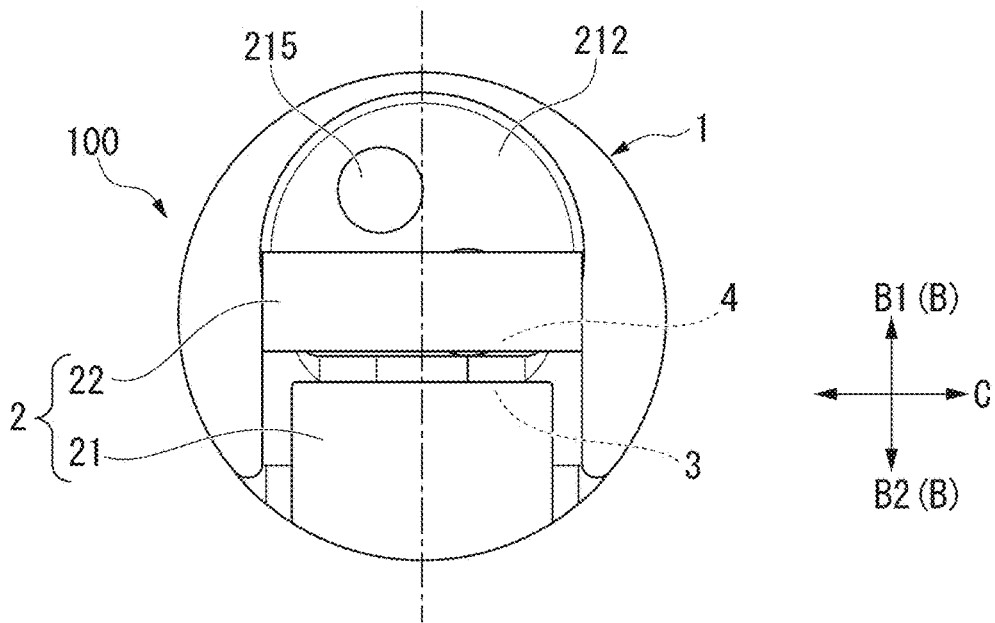
FIG. 6 is a front view of the medical stapler in which the grasping part is in the closed state.

FIG. 5 is a perspective view of the medical stapler 100 in which the grasping part 2 is in the closed state. FIG. 6 is a front view of the medical stapler 100 in which the grasping part 2 is in the closed state.

When the cap 1 is attached to the distal end part 211 of the endoscope 200, the objective lens 215 and the forceps mouth 214 are exposed from the opening 13 on the distal end side in the first through hole 11 of the cap 1, as shown in FIGS. 5 and 6. Therefore, the practitioner can observe a treatment target with the objective lens 215 even in a state in which the medical stapler 100 is attached to the distal end part 211 of the endoscope 200.

Figure 7:
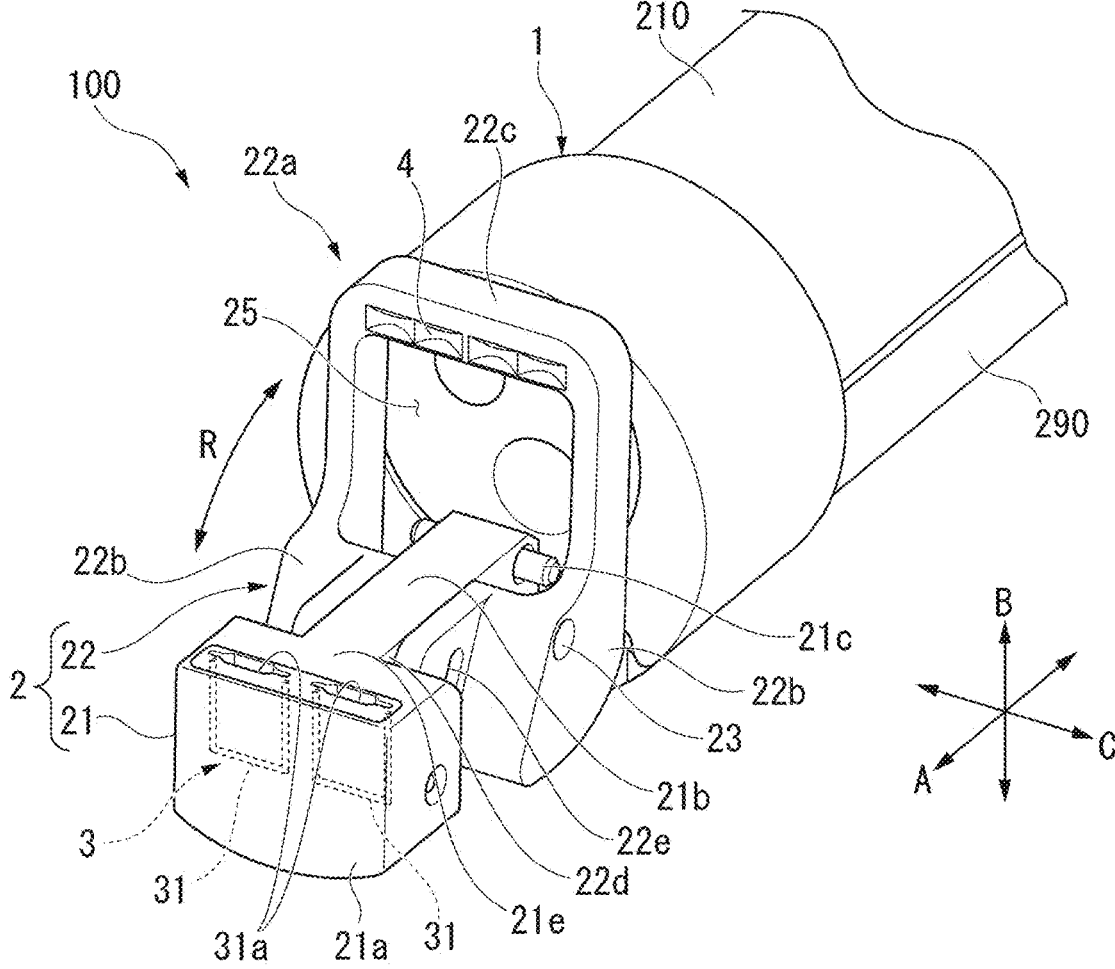
FIG. 7 is a perspective view of the medical stapler in which the grasping part is in an open state.
Figure 8:
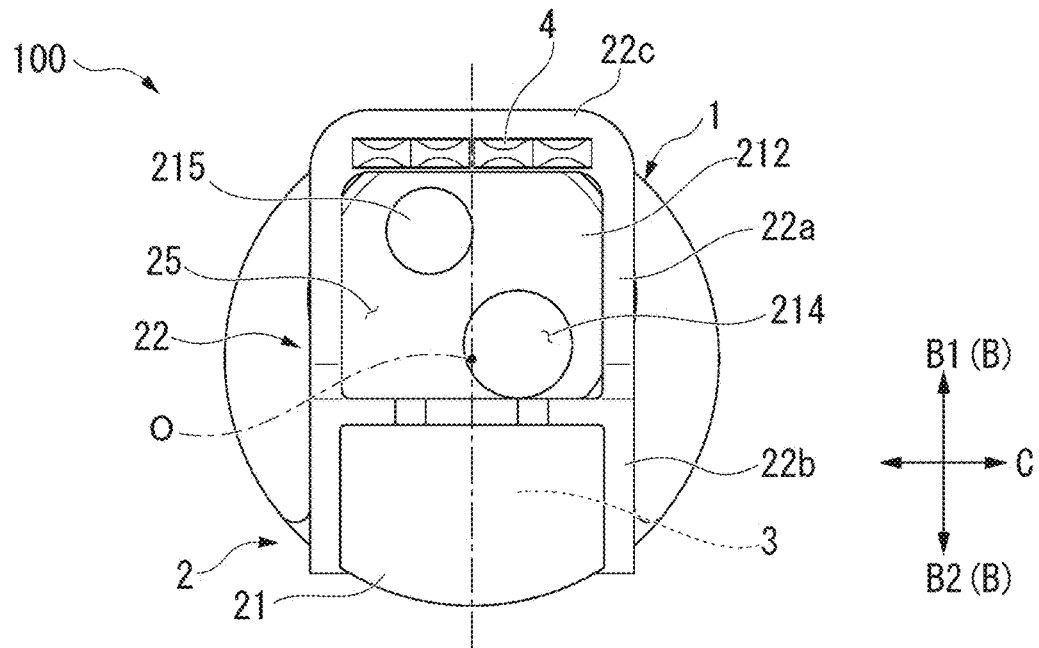
FIG. 8 is a front view of the medical stapler in which the grasping part is in the open state.

FIG. 7 is a perspective view of the medical stapler 100 in which the grasping part 2 is in the open state. FIG. 8 is a front view of a medical stapler 100 in which the grasping part 2 is in the open state.

Figure 9:
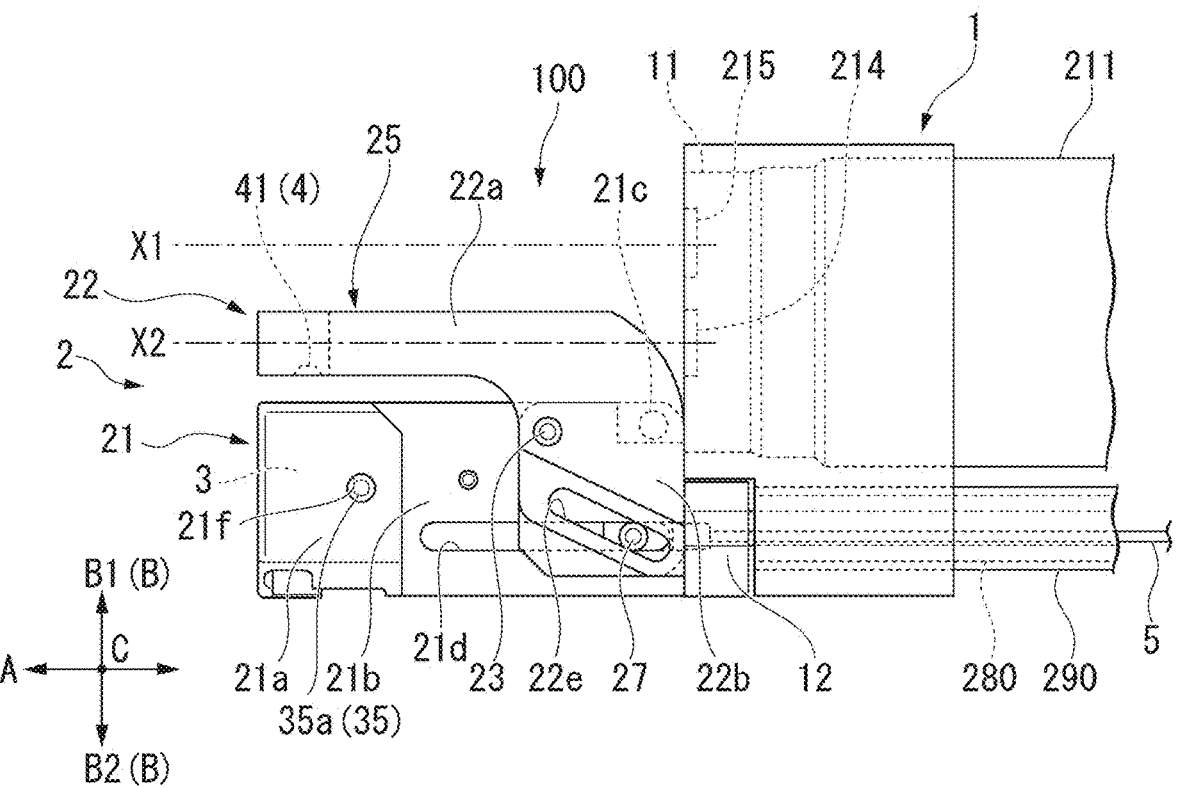
FIG. 9 is a side view of the medical stapler in which the grasping part is in the closed state.
Figure 10:
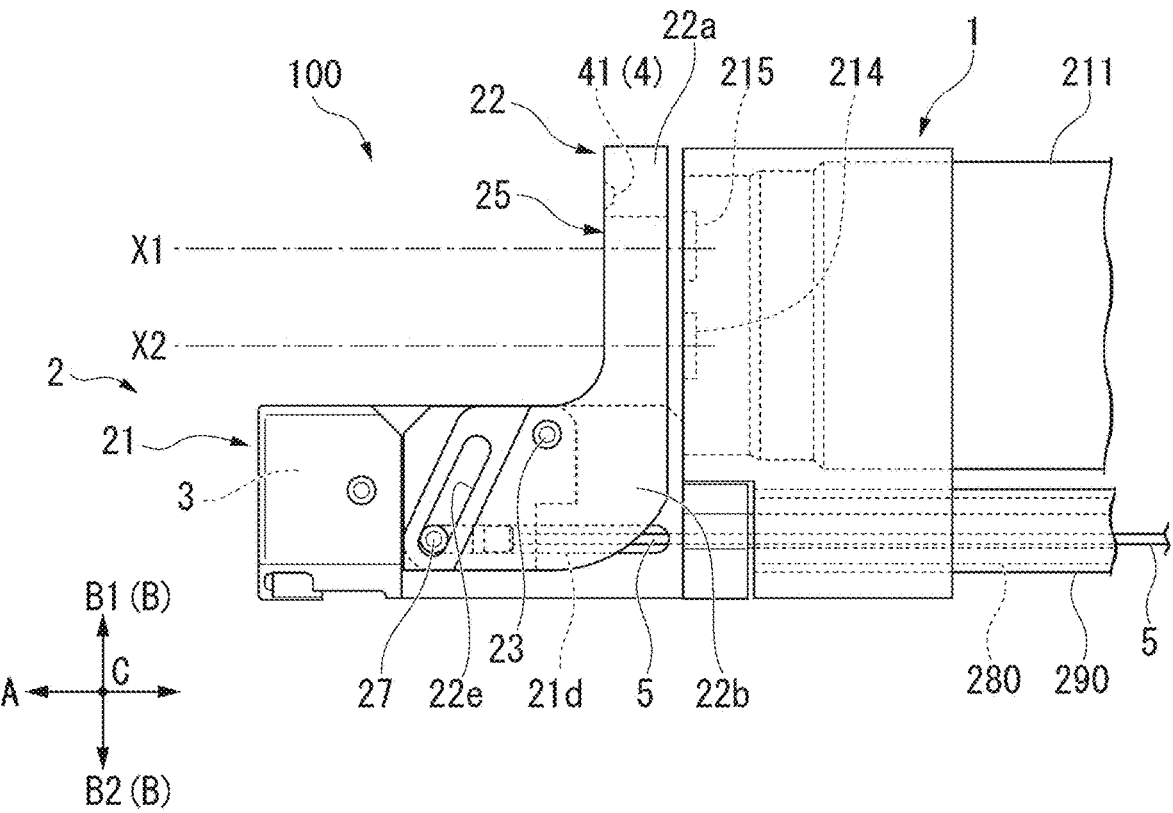
FIG. 10 is a side view of the medical stapler in which the grasping part is in the open state.

FIG. 9 is a side view of the medical stapler 100 in which the grasping part 2 is in the closed state. FIG. 10 is a side view of the medical stapler 100 in which the grasping part 2 is in the open state.

The grasping part 2 is provided on the distal end side of the cap 1 and a grasped target tissue can be sutured with the staple S. The grasping part 2 includes a first grasping member 21, a second grasping member 22, an opening/closing rotation shaft 23, and a movable pin 27.

The first grasping member 21 and the second grasping member 22 are connected so that they can be opened and closed by the opening/closing rotation shaft 23. The first grasping member 21 and the second grasping member 22 rotate relatively to grasp the target tissue.

The opening/closing rotation shaft 23 is provided on the distal end side of the cap 1. An axial direction (a width direction C) of the opening/closing rotation shaft 23 is perpendicular to the axial direction A and the vertical direction B of the cap 1. As shown in FIG. 8, the grasping part 2 is symmetrically formed with respect to the central axis in the vertical direction B passing through the central axis O of the cap 1.

Figure 11:
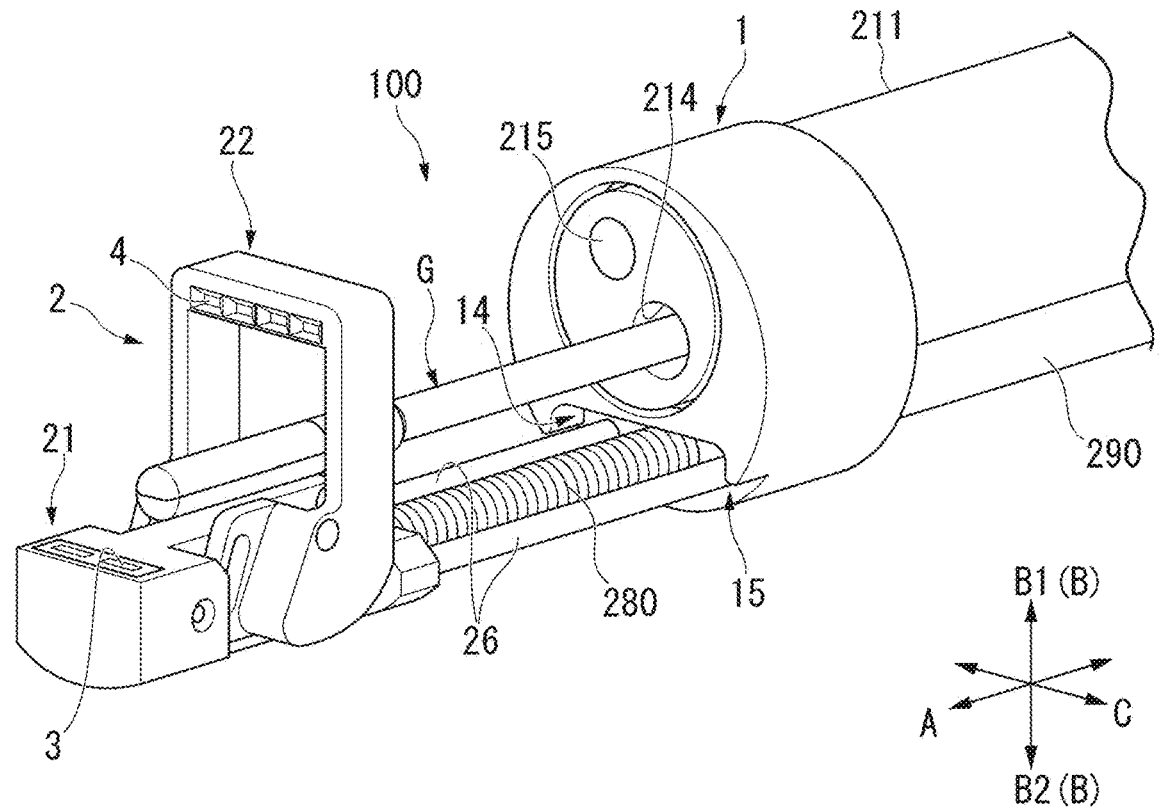
FIG. 11 is a perspective view showing a connection between a first grasping member and a cap.

FIG. 11 is a perspective view showing the connection between the first grasping member 21 and the cap 1.

The first grasping member 21 is connected to the distal end side of the cap 1 so that advance and retraction are possible. The first grasping member 21 is connected to the cap 1 in the downward direction B2 from the central axis O of the cap 1. Two support members 26 extending to the proximal end side in the axial direction A are attached to the first grasping member 21.

The two support members 26 are rigid long members and support the first grasping member 21 with respect to the cap 1 so that advance and retraction are possible. The two support members 26 are inserted into the third through hole 14 and the fourth through hole 15, respectively, so that advance and retraction are possible in the axial direction A. That is, the two support members 26, the third through hole 14, and the fourth through hole 15 constitute an advance/retraction mechanism of the first grasping member 21.

Because the first grasping member 21 is supported by the two support members 26 arranged in the width direction C, it does not rotate with the axial direction A as the rotation axis. Moreover, the two support members 26 suppress the deflection of the wire sheath 280 at the time of pulling the tissue in a pull-in step S16 to be described below and can support the first grasping member 21 of the grasping part 2 so that it does not move with respect to the central axis O2. When the rigidity of the support member 26 is sufficient, the support member 26 may be a single member.

As shown in FIG. 11, the distal end part of the wire sheath 280 through which the opening/closing manipulation wire 5 and the release manipulation wire 6 are inserted is fixed to the first grasping member 21. When the wire sheath 280 advances and retracts with respect to the resin sheath 290, the first grasping member 21 connected to the wire sheath 280 advances and retracts with respect to the cap 1.

As shown in FIG. 4, the first grasping member 21 is arranged at a position overlapping the second through hole 12 in the front view. Moreover, as shown in FIG. 8, the first grasping member 21 is arranged at a position that does not overlap the objective lens 215 and the forceps mouth 214 of the endoscope 200 in the front view.

As shown in FIG. 7, the first grasping member 21 has a first distal end part 21a and a first body part 21b and is formed in a substantially T-shaped shape in a plan view. The first distal end part 21a is arranged on the distal end side of the first body part 21b.

The first distal end part 21a is formed in a substantially rectangular parallelepiped. The first distal end part 21a is formed in a rectangular shape extending in the axial direction (the width direction C) of the opening/closing rotation shaft 23 in a plan view. The staple release part 3 is provided on the first distal end part 21a. The opening 31a of the staple release part 3 is provided on a surface of the first distal end part 21a in the upward direction B1 (an upper surface 21e).

The first body part 21b is an elongated member extending in the axial direction A. The distal end of the first body part 21b is fixed to the first distal end part 21a. The proximal end of the first body part 21b is fixed to the support member 26. The first body part 21b includes an abutting pin 21c and a first engagement groove 21d.

The abutting pin 21c is provided at the proximal end of the first body part 21b and is in contact with the second grasping member 22 in the closed state to regulate a movable range of the second grasping member 22.

As shown in FIG. 9, the first engagement groove 21d is a groove that penetrates in the axial direction C of the opening/closing rotation shaft 23 in the first body part 21b. The first engagement groove 21d extends in the axial direction A.

The second grasping member 22 is rotatably attached to the first grasping member 21 by the opening/closing rotation shaft 23. The second grasping member 22 includes a U-shaped member 22a formed in a substantially U-shaped shape and a second body part 22b that rotatably supports the U-shaped member 22a.

The U-shaped member 22a is formed in a substantially U-shaped shape, both end parts are connected to the second body part 22b, and a central part is arranged on the distal end side. The central part has a second distal end part 22c. The second distal end part 22c is formed in a substantially rectangular parallelepiped. The staple accommodation part 4 is provided on the second distal end part 22c.

The second body part 22b is rotatably attached to the first body part 21b of the first grasping member 21 by the opening/closing rotation shaft 23. A guide groove 22d into which the first body part 21b is inserted is formed in the second body part 22b. A second engagement groove 22e is formed on both sides of the guide groove 22d of the second body part 22b.

The second engagement groove 22e is a groove formed in the second body part 22b. The second engagement groove 22e is a groove that penetrates in the axial direction C. The second engagement groove 22e is formed on an opposite side of the staple accommodation part 4 across the opening/closing rotation shaft 23 in the side view. The second engagement groove 22e is formed symmetrically with respect to the central axis in the vertical direction B passing through the central axis O in the second grasping member 22.

As shown in FIG. 7, the second grasping member 22 has a visual field space 25 that penetrates in an opening/closing direction R between the staple accommodation part 4 on the distal end side and the opening/closing rotation shaft 23 on the proximal end side. In the present embodiment, the visual field space 25 is a space surrounded by the edges of the U-shaped member 22a formed in a substantially U-shaped shape.

The movable pin 27 is engaged in the first engagement groove 21d and the second engagement groove 22e and advances and retracts in the axial direction A along the first engagement groove 21d. The distal end of the opening/closing manipulation wire 5 is attached to the movable pin 27. As shown in FIG. 10, the opening/closing manipulation wire 5 advances to the distal end side, such that the movable pin 27 rotates the second grasping member 22 around the opening/closing rotation shaft 23, and the grasping part 2 is in the open state.

The opening/closing manipulation wire 5 retracts to the proximal end side, such that the movable pin 27 rotates the second grasping member 22 around the opening/closing rotation shaft 23, and the grasping part 2 is in the closed state as shown in FIG. 9. That is, the opening/closing manipulation wire 5 is a member that transmits a power force for causing the grasping part 2 to grasp the target tissue by rotating the first grasping member 21 and the second grasping member 22 relatively.

When the grasping part 2 is in the closed state, the staple release part 3 and the staple accommodation part 4 face each other in the vertical direction B as shown in FIG. 6. When the grasping part 2 is in the closed state, a slight gap is formed between the staple release part 3 and the staple accommodation part 4.

When the grasping part 2 is in the closed state, an optical axis X1 of the objective lens 215 passes through the outer sides of the first grasping member 21 and the second grasping member 22 as shown in FIGS. 5, 6, and 9. Moreover, when the grasping part 2 is in the closed state, a central axis X2 of the forceps mouth 214 does not overlap the first grasping member 21 in the front view, but is in a position that overlaps the second grasping member 22.

When the grasping part 2 is in the open state, the staple accommodation part 4 is arranged on the proximal end side of the opening/closing rotation shaft 23 as shown in FIG. 10. When the grasping part 2 is in the open state, the staple release part 3 and the staple accommodation part 4 are arranged on both sides with the optical axis X1 of the objective lens 215 sandwiched therebetween as shown in FIGS. 7, 8, and 10.

When the grasping part 2 is in the open state, the optical axis X1 of the objective lens 215 passes through the visual field space 25. Moreover, when the grasping part 2 is in the open state, the central axis X2 of the forceps mouth 214 passes through the visual field space 25.

Figures 12, 13:
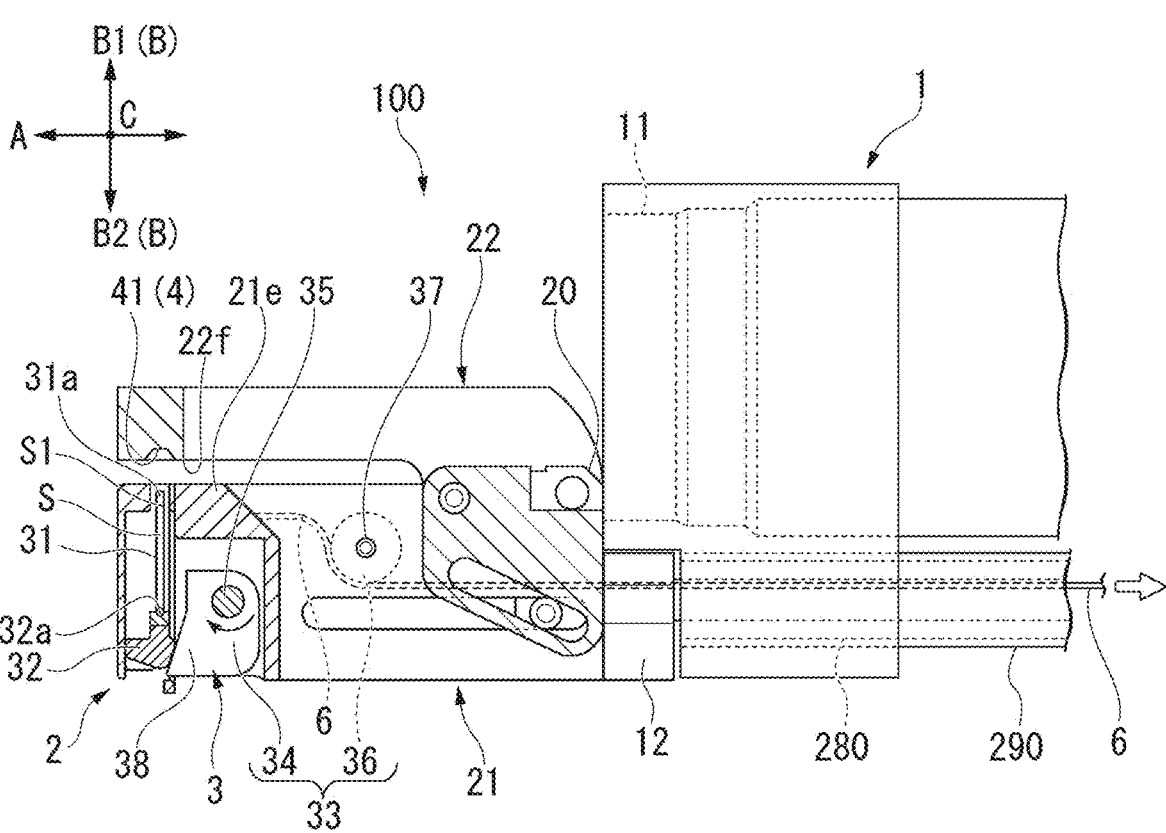
FIG. 12 is a cross-sectional view of the grasping part including a staple release part.
FIG. 13 is a cross-sectional view of the grasping part after a release manipulation wire is pulled.

FIG. 12 is a cross-sectional view of the grasping part 2 including the staple release part 3.

The staple release part 3 can be provided in the first distal end part 21a of the first grasping member 21 and can store and release the staple S. The staple release part 3 includes a staple storage part 31, a straight-moving member (a support member) 32, and a rotation member (an extrusion member) 33.

The staple storage part 31 is a space for storing the staple S provided in the first distal end part 21a of the first grasping member 21. As shown in FIG. 7, two staple storage parts 31 can be formed side by side in a width direction C in the first grasping member 21 and two U-shaped staples S can be stored.

The staple storage part 31 is open in the upward direction B1 in the opening 31a formed in the upper surface 21e of the first distal end part 21a. The staple S is stored in the staple storage part 31 from the opening 31a. The staple S is stored in the staple storage part 31 in a state in which the needle tip S1 of the staple S is directed in the upward direction B1.

The staple storage part 31 is formed in a substantially rectangular shape in which a short side extends in the axial direction A and a long side extends in the width direction C in a plan view. In the staple S accommodated in the staple storage part 31, the needle tips S1 at both ends are arranged in the width direction C.

The straight-moving member (the support member) 32 is a member accommodated in the staple storage part 31 and the internal space of the staple storage part 31 can be moved in the vertical direction B. The straight-moving member 32 has a concave part 32a that supports the staple S from the downward direction B2. The staple S stored in the staple storage part 31 is fitted into the concave part 32a.

A first pulley (a first member) 34 and a second pulley 36 included in the rotation member 33 are rotatably attached to inner sides of the first grasping member 21, and the first pulley 34 and the second pulley 36 move the straight-moving member 32 in the vertical direction B by performing a rotation operation. The distal end of the release manipulation wire 6 is connected to the first pulley 34. By pulling the release manipulation wire 6, the first pulley 34 can be rotated.

The second pulley 36 is rotatably attached to an inner side of the first grasping member 21 and the first pulley 34 is arranged on the distal end side of the second pulley 36. A rotation shaft 35 of the first pulley 34 and a rotation axis 37 of the second pulley 36 extend in the width direction C and are substantially parallel to the opening/closing rotation shaft 23 of the grasping part 2. The first pulley 34 has a convex part (an abutting part) 38 that supports the straight-moving member 32 on the distal end side from the downward direction B2.

The distal end of the release manipulation wire 6 is connected in the upward direction B1 of the rotation shaft 35 in the first pulley 34. The release manipulation wire 6 passes through the second through hole 12 via the second pulley 36 from the first pulley 34 and extends to the release manipulation part 270.

The second pulley 36 is provided to adjust the position so that the release manipulation wire 6 can be guided to the second through hole 12 without difficulty and to reduce the frictional resistance when the release manipulation wire 6 is guided to the second through hole 12. Therefore, a similar effect can be obtained even if only the first pulley 34 is used as the rotation member 33 and a member that reduces friction is provided as a part having good sliding properties having an R shape instead of the second pulley 36.

FIG. 13 is a cross-sectional view of the grasping part 2 after the release manipulation wire 6 is pulled.

When the release manipulation wire 6 is pulled, the first pulley 34 rotates to the proximal end side in the upward direction B1 with the rotation shaft 35 as a rotation center and the first pulley 34 rotates to the distal end side in the downward direction B2. As a result, a convex part 38 of the first pulley 34 pushes the straight-moving member 32 in the upward direction B1 and the stored staple S is released from the opening 31a in the upward direction B1. That is, the release manipulation wire 6 is a member that transmits motive power for causing the staple S to be released to the grasping part 2. The rotation member 33 is an injection mechanism capable of injecting the staple S.

The staple accommodation part 4 is provided on the lower surface 22f of the second distal end part 22c of the second grasping member 22. A plurality of pockets 41 capable of accommodating the staple S released from the staple release part 3 are provided in the staple accommodation part 4. In the present embodiment, because two U-shaped staples are released from the staple release part 3, four pockets are provided in the staple accommodation part 4. When the grasping part 2 is in the closed state, the opening 31a from which the staple S is released and the pocket 41 of the staple accommodation part 4 are facing in the vertical direction B as shown in FIG. 12.

Figure 14:
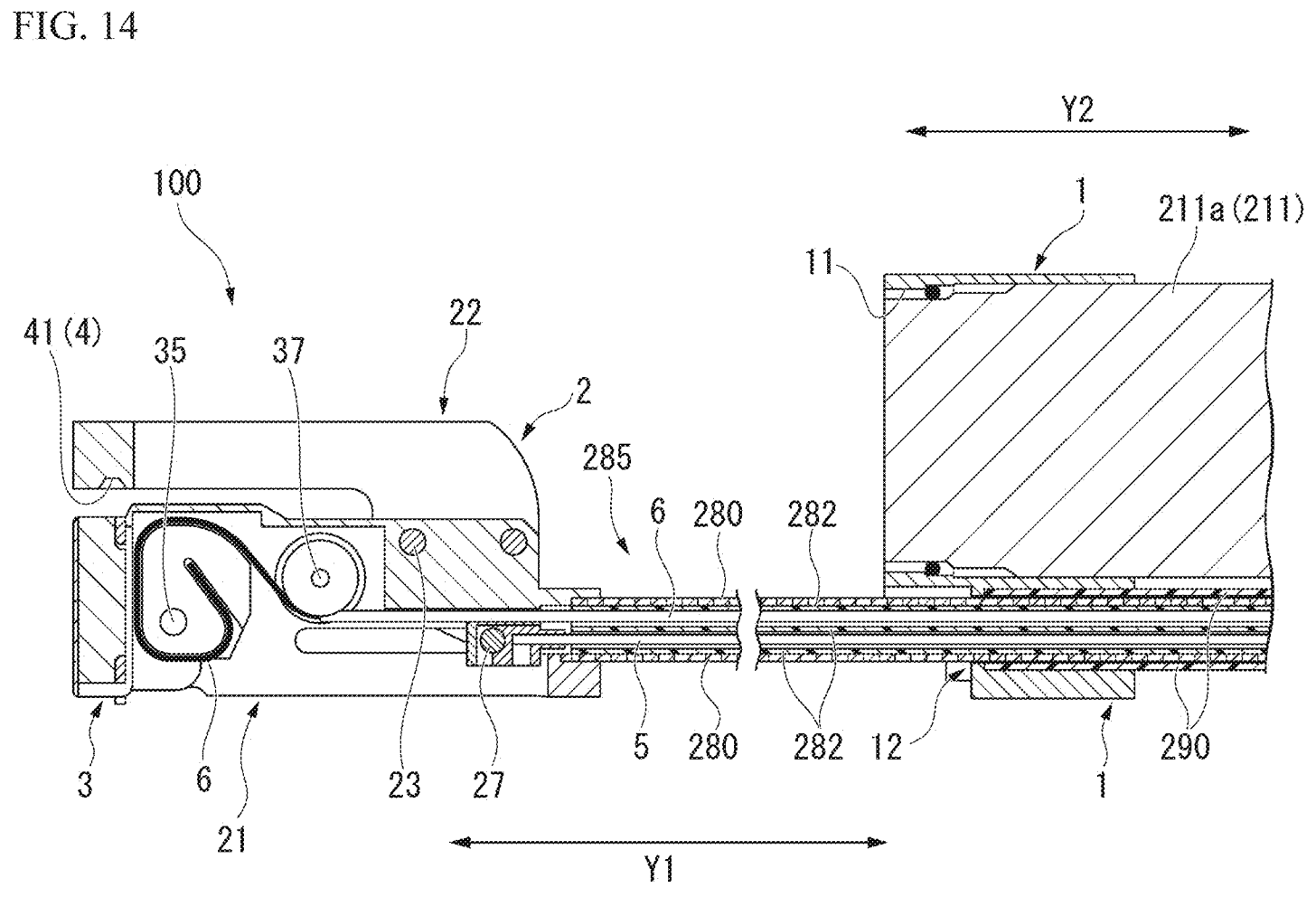

FIG. 14 is a cross-sectional view of the cap 1 and the grasping part 2 that has advanced.

The grasping part 2 is connected to the opening/closing manipulation wire 5 and the release manipulation wire 6 inserted through the wire sheath 280 even in the advanced state. The practitioner can advance and retract the opening/closing manipulation wire 5 and the release manipulation wire 6 even in a state in which the grasping part 2 has advanced.

The grasping part 2 shown in FIG. 14 is arranged at the most advanced position with respect to the cap 1. In the wire sheath 280, a length Y1 of the distal end part 285 capable of projecting from the second through hole 12 of the cap 1 to the distal end side is shorter than or equal to a length Y2 of the hard part 211a in the distal end part 211 of the endoscope 200.

[Operation of Medical Stapler 100]

Next, an example of an operation of the medical stapler 100 will be described.

Figure 15:
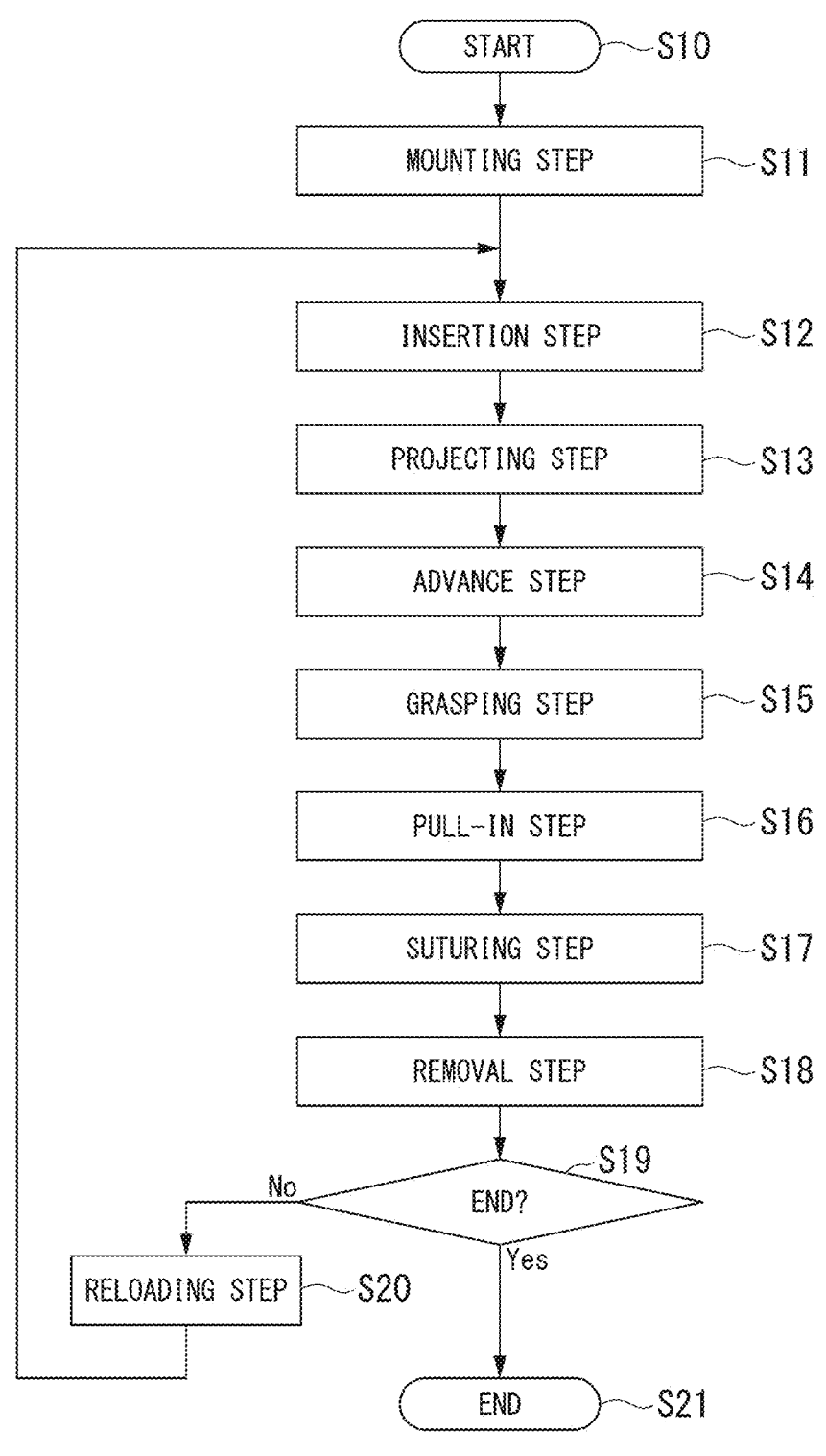
FIG. 15 is a flowchart showing a manipulation procedure using the medical stapler by a practitioner.

FIG. 15 is a flowchart showing a manipulation procedure using the medical stapler 100 by the practitioner. FIGS. 16 to 19 are explanatory views showing the operation of the medical stapler 100.

First, the practitioner starts a manipulation using the medical stapler 100 (step S10). Subsequently, the practitioner performs a mounting step S11. In the mounting step S11, the practitioner attaches the medical stapler 100 to the distal end part 211 of the endoscope 200.

Subsequently, the practitioner performs an insertion step S12. In the insertion step S12, the practitioner inserts the medical stapler 100 and the endoscope 200 into the body.

Moreover, the practitioner moves the distal end part 211 of the endoscope 200, to which the medical stapler 100 is attached, toward a treatment target T (an example of a target tissue). The practitioner manipulates the opening/closing manipulation part 250 and advances the opening/closing manipulation wire 5 to make the grasping part 2 open. Because the optical axis X1 of the objective lens 215 passes through the visual field space 25, the practitioner can observe the treatment target T via the imaging unit of the endoscope 200.

Figure 16:
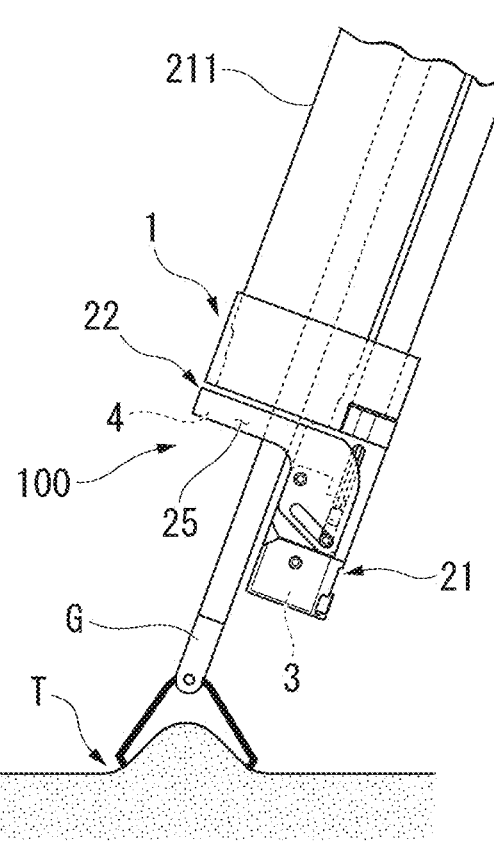
FIG. 16 is a diagram showing an operation of a projecting step of the medical stapler.

FIG. 16 is a view showing an operation of a projecting step S13 of the medical stapler 100.

The practitioner performs the projecting step S13 and projects a grasping forceps (a treatment tool) G from the forceps mouth 214. In the projecting step S13, because the central axis X2 of the forceps mouth 214 passes through the visual field space 25, the practitioner can project the grasping forceps G from the forceps mouth 214 as shown in FIGS. 11 and 16.

Figure 17:
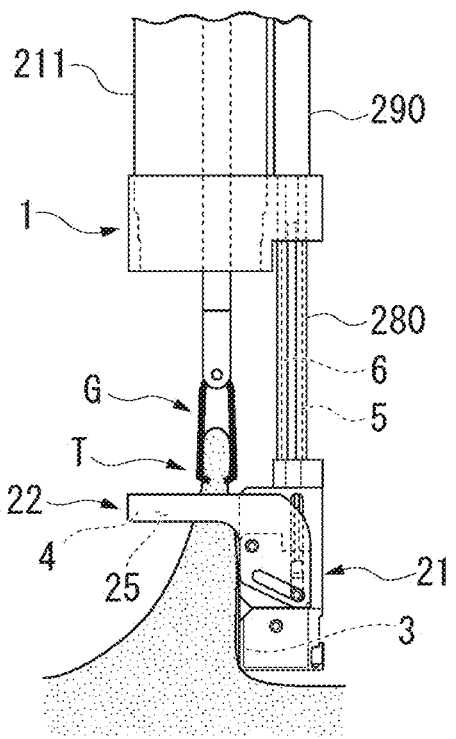
FIG. 17 is a diagram showing operations of an advance step, a grasping step, and a pull-in step of the medical stapler.

FIG. 17 is a view showing operations of an advance step S14, a grasping step S15, and the pull-in step S16 of the medical stapler 100.

When the treatment target T is in a place that the endoscope 200 cannot easily access, the practitioner performs the advance step S14 and advances the grasping part 2 by advancing the wire sheath 280 as shown in FIG. 17.

Moreover, the practitioner performs the grasping step S15, and grasps the treatment target T by projecting the grasping forceps G from the visual field space (the penetration space) 25 of the grasping part 2 that has advanced.

Next, the practitioner performs the pull-in step S16 and retracts the grasping forceps G in a state in which the treatment target T is grasped by the grasping forceps G as shown in FIG. 17. The practitioner pulls the treatment target T until the treatment target T passes through the visual field space (the penetration space) 25 by retracting the grasping forceps G until the distal end of the grasping forceps G passes through the visual field space (the penetration space) 25.

As a result, the treatment target T is arranged on the proximal end side of the staple release part 3. The practitioner may pull the treatment target T by advancing the grasping part 2 with respect to the grasping forceps G. That is, the grasping forceps G is relatively retracted with respect to the grasping part 2 and the treatment target T is pulled.

Here, as shown in FIG. 17, because the first grasping member 21 suppresses the peripheral portion of the treatment target T, the practitioner easily pulls the treatment target T with the grasping forceps G.

In addition, the advance step S14 may be performed before the grasping step S15 or before the pull-in step S16. In either case, in the pull-in step S16, the first grasping member 21 can suppress a peripheral part of the treatment target T.

Figure 18:
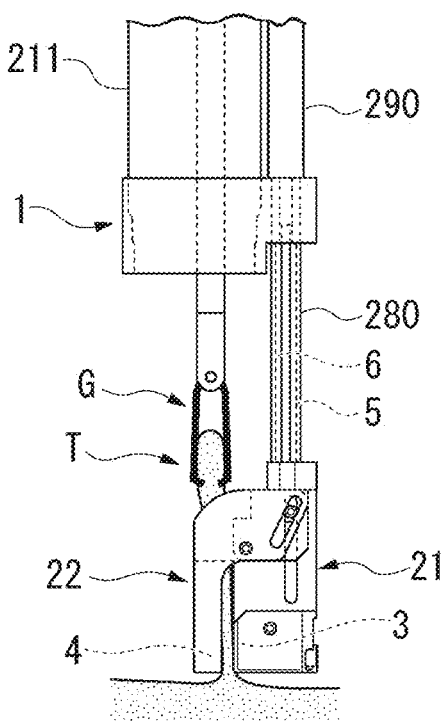
FIG. 18 is a diagram showing an operation of a suturing step of the medical stapler.

FIG. 18 is a diagram showing an operation of the suturing step S17 of the medical stapler 100.

The practitioner performs the suturing step S17 and manipulates the opening/closing manipulation part 250 to retract the opening/closing manipulation wire 5 and cause the grasping part 2 to be closed as shown in FIG. 18. The treatment target T is sandwiched between the staple release part 3 of the first grasping member 21 and the staple accommodation part 4 of the second grasping member 22.

When the grasping part 2 is in the closed state, because a part of the treatment target T grasped by the grasping forceps G can be stored in the space (the visual field space 25) formed by the U-shaped member 22a and the second body part 22b of the second grasping member 22, the treatment target T clamped between the staple release part 3 and the staple accommodation part 4 is easily fixed When the grasping part 2 is in the closed state, the optical axis X1 of the objective lens 215 passes through the outer sides of the first grasping member 21 and the second grasping member 22 as shown in FIG. 9. Therefore, even if the grasping part 2 is in the closed state, the practitioner can observe the treatment target T via the imaging unit of the endoscope 200.

As shown in FIG. 18, the practitioner manipulates the release manipulation part 270 in a state in which the treatment target T is sandwiched between the staple release part 3 and the staple accommodation part 4, pulls the release manipulation wire 6, and releases the stored staple S toward the staple accommodation part 4. The needle tip S1 of the staple S penetrates through the treatment target T and bends due to contact with the pocket 41 of the staple accommodation part 4. As a result, the treatment target T is sutured by the staple S.

Figure 19:
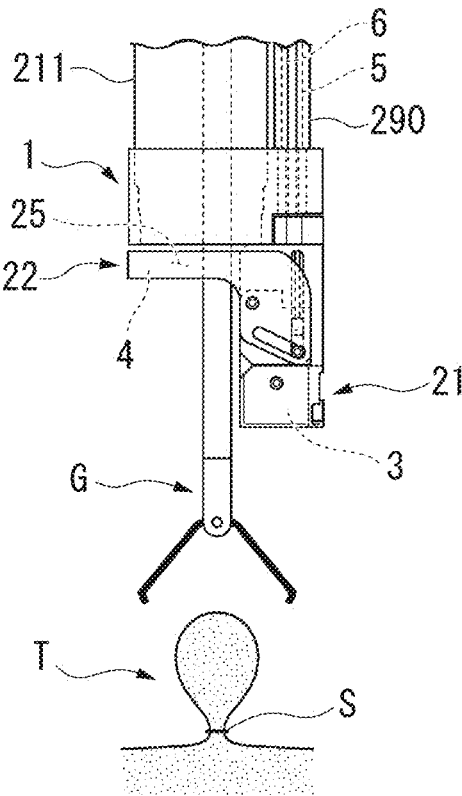
FIG. 19 is a diagram showing an operation of a removal step of the medical stapler.

FIG. 19 is a view showing an operation of the removal step S18 of the medical stapler 100.

The practitioner performs the removal step S18 and manipulates the opening/closing manipulation part 250, such that the grasping part 2 is in the open state again as shown in FIG. 19. The practitioner completes the suturing treatment by moving the grasping forceps G away from the treatment target T. The practitioner removes the medical stapler 100 and the endoscope 200 from the body.

In addition, in the insertion step S12 and the removal step S18, the practitioner arranges the grasping part 2 at the most retracted position so that the medical stapler 100 easily passes through the body.

Subsequently, the practitioner determines whether or not to end the manipulation (step S19). When the manipulation is not ended, the practitioner performs the reloading step S20. For example, when all of the treatment target T cannot be sutured in the suturing step S17, the practitioner does not end the manipulation and performs the reloading step S20. In the reloading step S20, the practitioner reloads the staple S into the medical stapler 100 removed from the body. At this time, the practitioner reloads the cartridge 30 having the staple storage part 31.

Here, the cartridge 30 will be described. The operation in the reloading step S20 will be described below.

Figure 20:
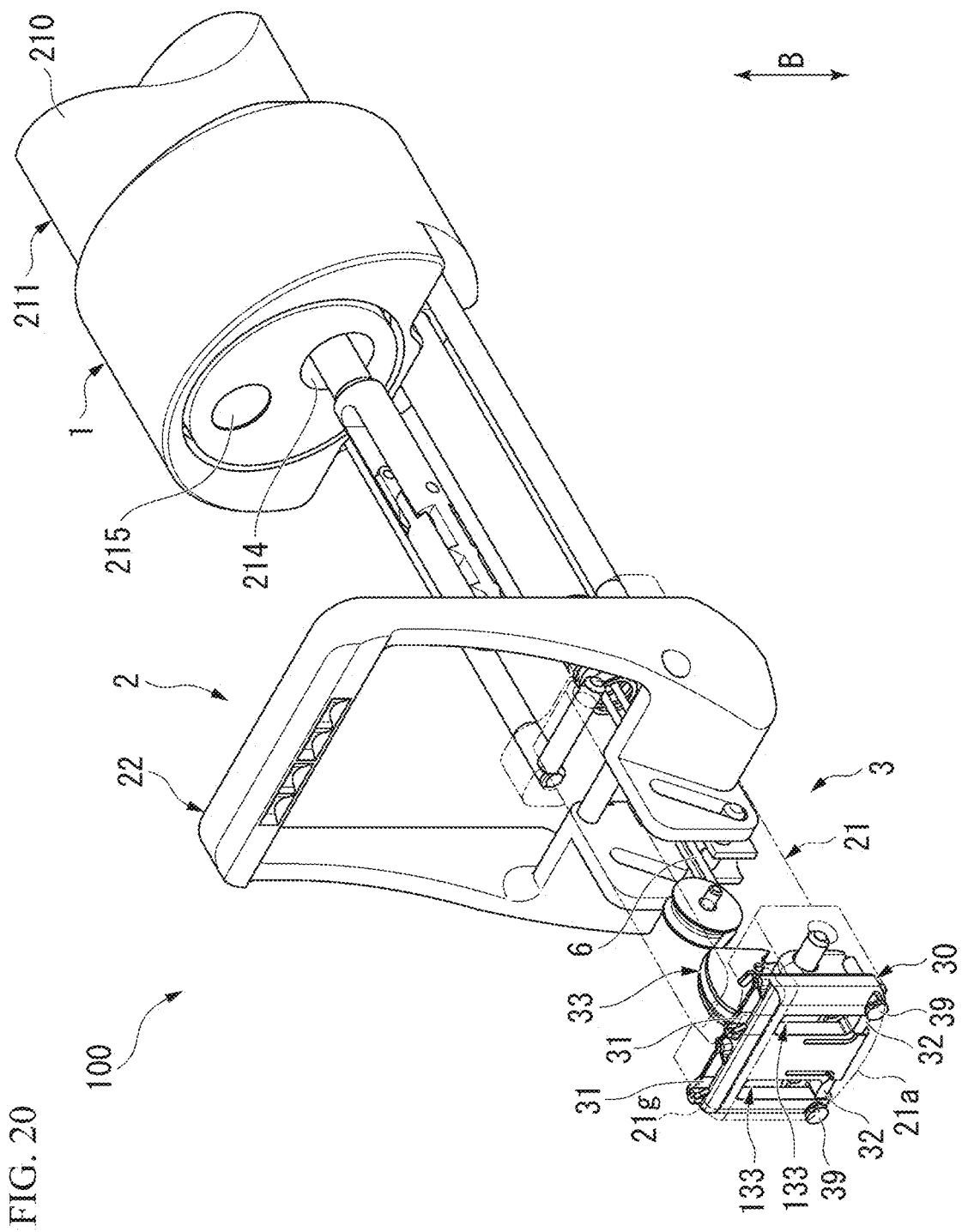
FIG. 20 is a perspective view showing a configuration of the medical stapler.
Figure 21:
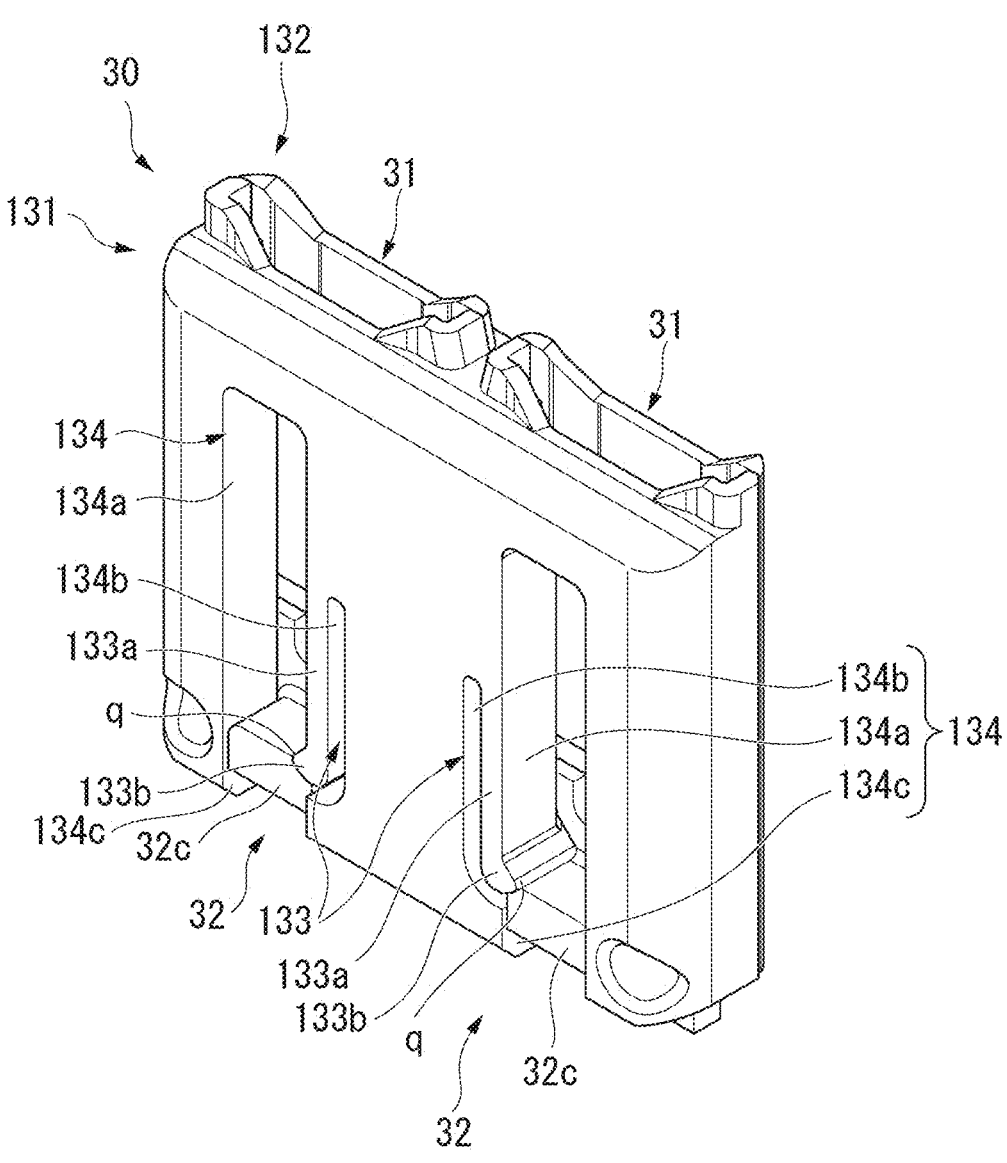
FIG. 21 is a perspective view showing a configuration of a cartridge.
Figure 21:
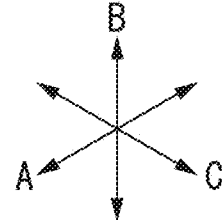
Figure 22:
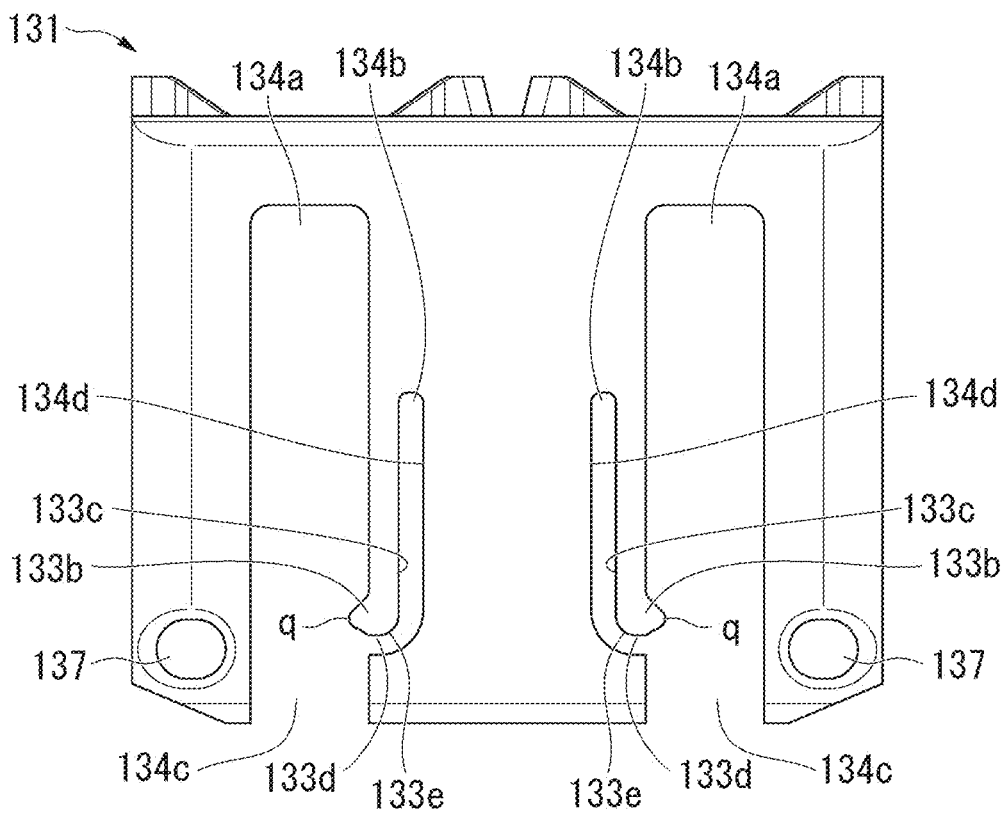
FIG. 22 is a front view showing a configuration of a first member of the cartridge.
Figure 22:
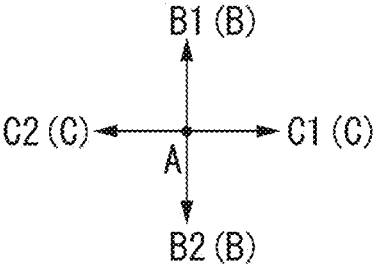
Figure 23:
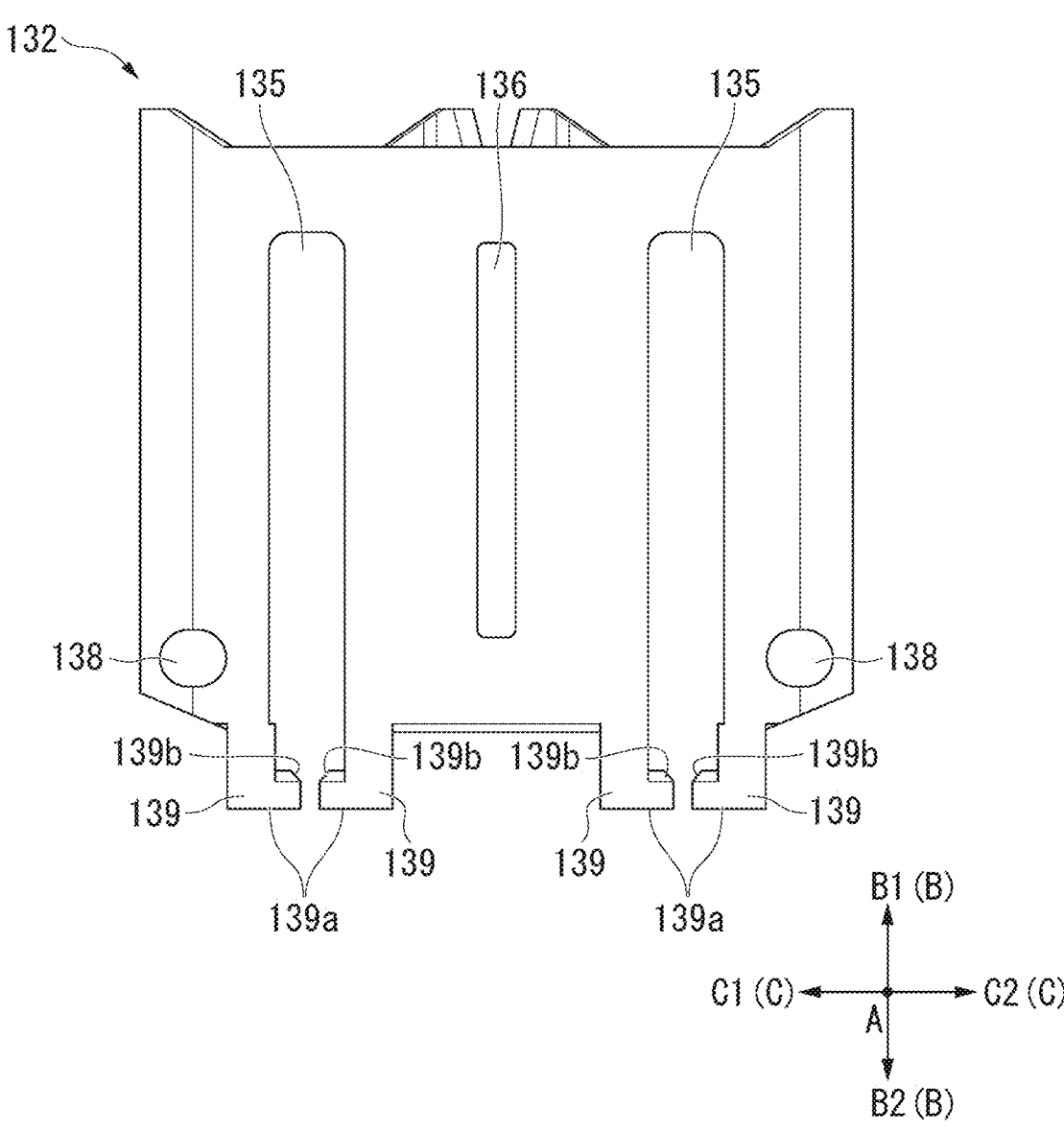
FIG. 23 is a front view showing a configuration of a second member of the cartridge.
Figure 24:
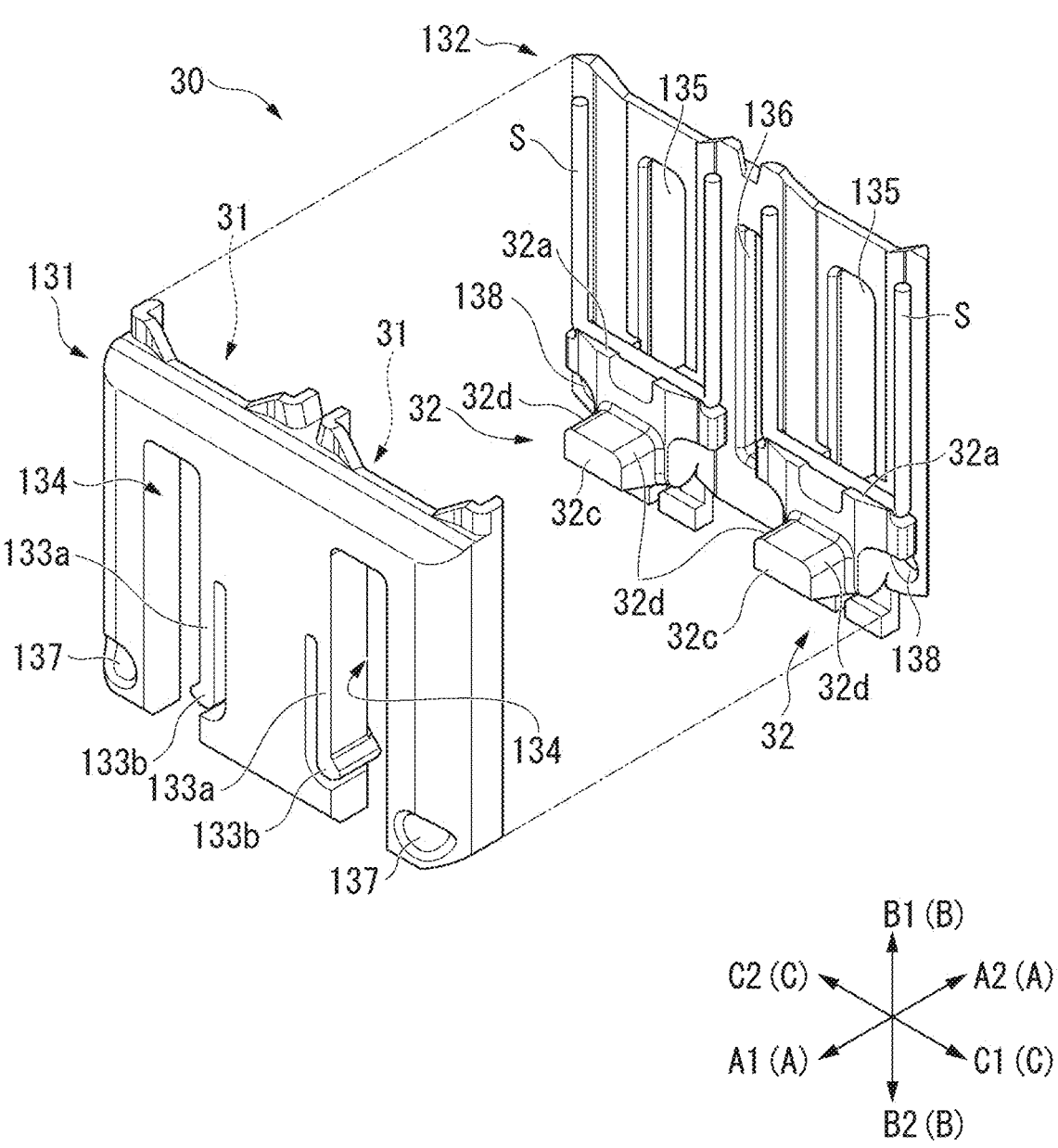
FIG. 24 is an exploded perspective view showing a configuration of the cartridge.
Figure 25:
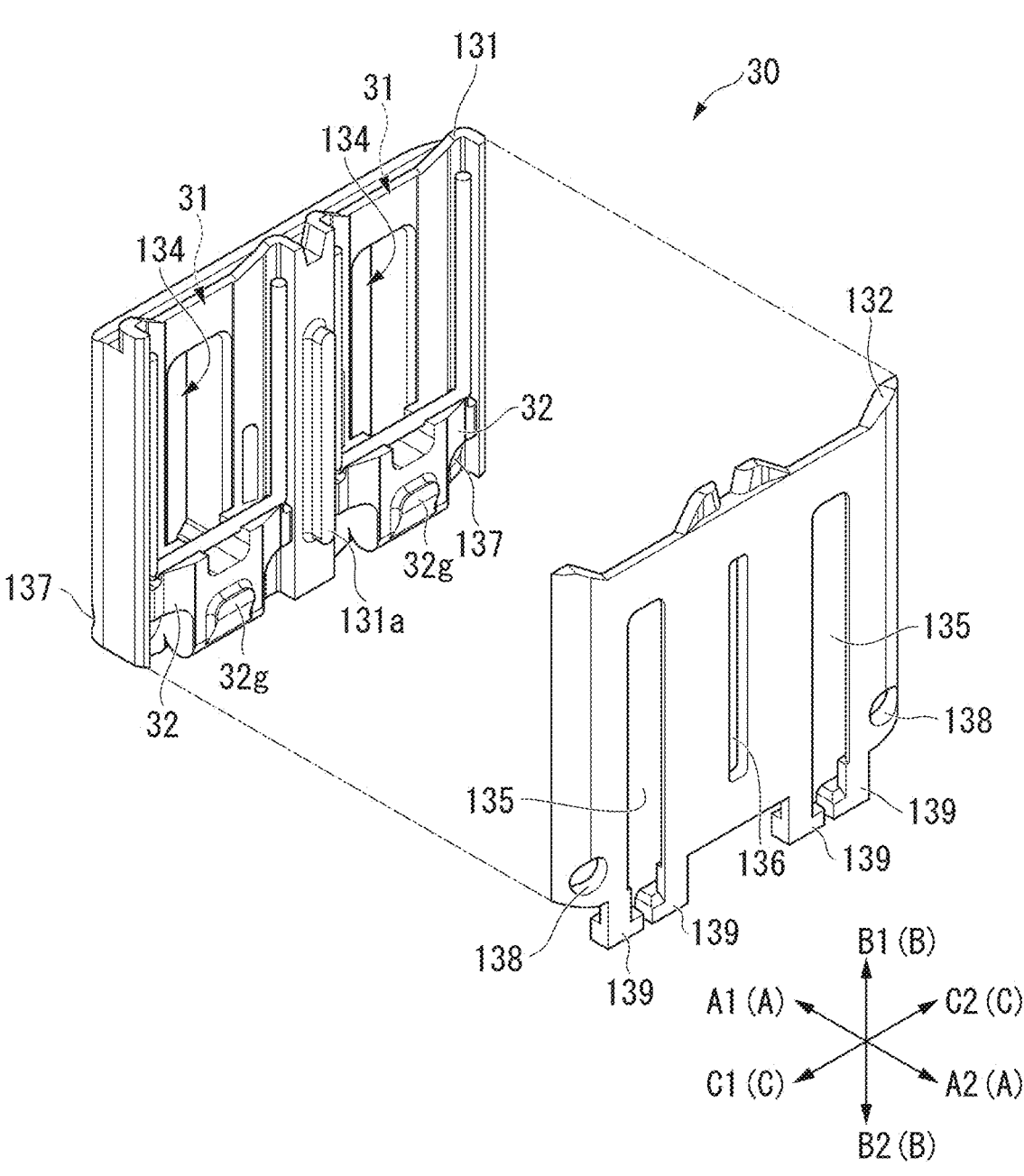
FIG. 25 is an exploded perspective view showing the configuration of the cartridge.

FIG. 20 is a perspective view showing a configuration of the medical stapler 100. FIG. 21 is a perspective view showing a configuration of the cartridge 30. FIG. 22 is a front view showing a configuration of the first member 131 of the cartridge 30. FIG. 23 is a front view showing a configuration of the second member 132 of the cartridge 30. FIGS. 24 and 25 are exploded perspective views showing the configuration of the cartridge 30.

As shown in FIG. 20, the staple release part 3 includes the cartridge 30 having the staple storage part 31. The cartridge 30 is a member removably provided on the first distal end part 21a of the first grasping member 21, and is separate from the first grasping member 21.

The cartridge 30 is inserted into a concave part 21g formed in the first distal end part 21a of the first grasping member 21 from the upward direction B1. The cartridge 30 has a pair of staple storage parts 31 in the width direction C and the staples S are inserted into the staple storage parts 31, respectively.

As shown in FIG. 21, the cartridge 30 includes a first member 131 and a second member 132.

As shown in FIG. 21, the first member 131 has a pair of snap-fit parts 133 and a pair of through holes 134 at positions corresponding to the pair of staple storage parts 31.

The snap-fit part 133 has a snap-fit 133a provided inside of the pair of through holes 134 in the width direction C. The snap-fit 133a has a thin rod shape extending in the vertical direction B and a locking portion 133b projecting outward in the width direction C is formed on the downward direction B2 side.

The locking portion 133b forms a triangular shape as seen in the axial direction A and a top part q most projecting in the width direction C is formed in a non-sharp shape. Both outer surfaces of the locking portion 133b in the width direction C are chamfered and a connection surface 133e, which is a smooth curved surface connecting an outer surface 133c and a lower end surface 133d, is formed.

The through hole 134 penetrates through the first member 131 in a thickness direction. The through hole 134 includes a first through hole 134a formed on an outer side of the snap-fit 133a in the width direction C, a second through hole 134b formed on an inner side of the snap-fit 133a in the width direction C, and a third through hole 134c formed in the downward direction B2 of the snap-fit 133a in the first member 131.

The first through hole 134a longer than the second through hole 134b is formed along the vertical direction B. An upper end side of the first through hole 134a does not reach an upper surface of the cartridge 30. A lower end side of the first through hole 134a communicates with the third through hole 134c.

The second through hole 134b is connected to the inner sides of the first through hole 134a and the third through hole 134c in the width direction C in the downward direction B2 of the snap-fit 133a. The third through hole 134c communicating with the first through hole 134a in the vertical direction B is open on the lower surface of the first member 131.

The first through hole 134a and the third through hole 134c are guide holes for guiding the inserted straight-moving member 32 in the vertical direction B. A length of a combination of the first through hole 134a and the third through hole 134c in the vertical direction B is the same as or slightly longer than a movement range of the straight-moving member 32 in the vertical direction B.

The second through hole 134b is a through hole that forms a gap for allowing the displacement of the snap-fit 133a in the width direction C. In the second through hole 134b, the length in the vertical direction B is shorter than that of the first through hole 134a. The width of the second through hole 134b in the width direction C is substantially equal to or slightly smaller than the width of the snap-fit 133a.

The width of the second through hole 134b is preferably a width in which the snap-fit 133a displaced in the width direction C is not in contact with an inner surface 134d of the second through hole 134b when the straight-moving member 32 passes through the locking portion 133b of the snap-fit 133a in the vertical direction B.

As shown in FIGS. 21 and 24, the projection part 32c of the straight-moving member 32 is inserted into the third through hole 134c. The projection part 32c is a prism-shaped convex part projecting in a forward direction A1 of the axial direction A in the straight-moving member 32, and is in contact with a lower end of the snap-fit 133a from the downward direction B2 side.

The projection part 32c of the straight-moving member 32 has a substantially rectangular shape as seen from the forward direction A1 side and a pair of corners on the upward direction B1 side are subjected to R chamfering. The R surface 32d of the projection part 32c is in contact with the locking portion 133b of the snap-fit 133a located in the upward direction B1 from the downward direction B2 side.

A projection length along the projection part 32c in the axial direction A is substantially equal to a plate thickness of the snap-fit 133a. The projection length along the projection part 32c in the axial direction A and the plate thickness of the snap-fit 133a may have dimensions different from each other as long as the rigidity of both can be secured.

As shown in FIG. 23, the second member 132 has a pair of through holes 135 (slits) and a positioning hole 136 formed between these pairs of through holes 135 at positions corresponding to the pair of staple storage parts 31. Moreover, as shown in FIGS. 24 and 25, the second member 132 is arranged on a rearward direction A2 side of the first member 131 in the axial direction A.

The through hole 135 is formed at a position facing the through hole 134 of the first member 131 in the axial direction A. The through hole 135 penetrates through the second member 132 in the thickness direction. The through hole 135 long in the vertical direction B is formed and is substantially equal to a length of a combination of the first through hole 134a and the third through hole 134c of the first member 131. The through hole 135 opens on the lower surface of the second member 132. As shown in FIG. 25, a projection part 32g projecting from the straight-moving member 32 to the rearward direction A2 is inserted into the through hole 135.

As shown in FIG. 23, the positioning hole 136 is a hole thinner than the through hole 135 and formed with a shorter length than the through hole 135 in the vertical direction B. The positioning holes 136 are formed in the substantially center of the top, bottom, left, and right sides of the second member 132.

A positioning convex part 131a formed on an inner surface of the first member 131 (a surface facing the second member 132 as a surface of the rearward direction A2 side) is inserted into the positioning hole 136. The positioning hole 136 slightly larger than the above-described positioning convex part 131a is formed.

Moreover, a pushing part 139 is provided on both sides of the through hole 135 in the width direction C at the lower end of the through hole 135 open in the downward direction B2. The pushing part 139 has a substantial L-shaped shape projecting from the lower surface of the second member 132 in the downward direction B2 and bending toward the through hole 135 in the width direction C. As shown in FIG. 23, a dimension of the through hole 135 in the width direction C is narrowed at a part sandwiched between the pushing parts 139 in the width direction C.

A lower surface (a downward direction B2 surface) 139a of the pushing part 139 is a plane extending in the axial direction A and the width direction C. Moreover, at the distal end of the pushing part 139 bent in an L shape in the width direction C, a corner part in the upward direction B1 is chamfered and an inclined surface part 139b is formed. Therefore, the dimension of the through hole 135 of a part sandwiched between inclined surface parts 139b in the width direction C is narrowed in the downward direction B2. Moreover, the dimension of the through hole 135 of the portion sandwiched between the inclined surface parts 139b in the width direction C is smaller than the dimension of the convex part 38 of the first pulley 34 in the width direction C.

Moreover, the cartridge 30 is removably fixed to the first distal end part 21a of the first grasping member 21 via the connection member 39 inserted through the pair of insertion holes 137 formed on the lower end side of the first member 131 and the pair of insertion holes 138 formed on the lower end side of the second member 132. A method of fixing the cartridge 30 to the first grasping member 21 is not limited to this and the cartridge 30 may be removably provided on the first grasping member 21 using, for example, a snap-fit structure.

The operation in the reloading step S20 of the medical stapler 100 will be described with reference to FIGS. 26A to 26D and 27A to 27C. First, an operation of removing the cartridge 30 from the staple release part 3 will be described with reference to FIGS. 26A to 26D.

Figure 26A:
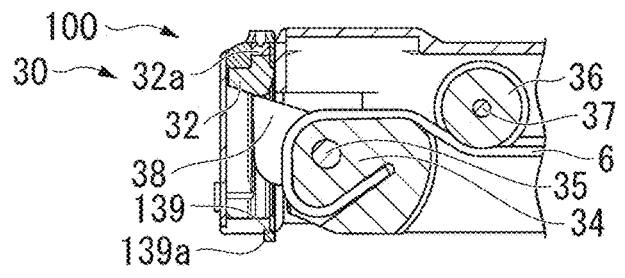
FIG. 26A is a cross-sectional view showing an operation in a reloading step of the medical stapler.
Figure 26A:
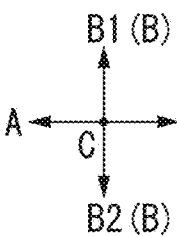

FIG. 26A is a cross-sectional view showing the operation in the reloading step S20 of the medical stapler 100. After the removal step S18, the medical stapler 100 shown in FIG. 26A is in a state after the staple S is ejected in the suturing step S17. Moreover, the medical stapler 100 is in a state in which it has been removed from the body in the removal step S18.

The medical stapler 100 shown in FIG. 26A is in a state in which the release manipulation wire 6 is pulled, the first pulley 34 is rotated, and the straight-moving member 32 is moved in the upward direction B1 by the convex part 38 of the first pulley 34. At this time, the convex part 38 of the first pulley 34 is inserted into the through hole 135 of the second member 132.

Figure 26B:
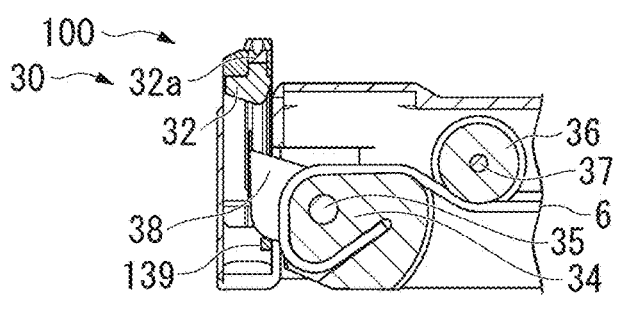
FIG. 26B is a cross-sectional view showing an operation following that of FIG. 26A in the reloading step of the medical stapler.
Figure 26B:
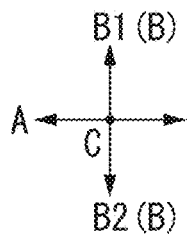

FIG. 26B is a cross-sectional view showing an operation following that of FIG. 26A in the reloading step S20 of the medical stapler 100. In the reloading step S20, the practitioner first removes the cartridge 30 from the first grasping member 21. At this time, when the cartridge 30 is fixed to the first grasping member 21 via the connection member 39, the practitioner removes the connection member 39 from the first grasping member 21 and the cartridge 30, and releases the fixation to the first grasping member 21 in the cartridge 30.

As shown in FIG. 26B, the practitioner moves the cartridge 30 in the upward direction B1 with respect to the first grasping member 21. At this time, the convex part 38 of the first pulley 34 moves the through hole 135 in the downward direction B2 with respect to the cartridge 30. The practitioner may grasp the cartridge 30 by hand to move the cartridge 30 or may move the cartridge 30 using a jig or the like.

As shown in FIG. 26B, when the cartridge 30 is moved in the upward direction B1 with respect to the first grasping member 21, the pushing part 139 of the second member 132 is in contact with the convex part 38, in a state in which the release manipulation wire 6 is pulled and rotated, in the downward direction B2.

When the practitioner further moves the cartridge 30 in the upward direction B1 from the state shown in FIG. 26B, the convex part 38 is pressed against each inclined surface part 139b of the pair of pushing parts 139 from the upward direction B1 in the second member 132. The pair of pushing parts 139 move in a direction away from the convex part 38 in the width direction C when the convex part 38 is pressed against the inclined surface part 139b from the upward direction B1. At this time, for example, the pushing part 139 moves in the width direction C according to the elasticity of the material.

The convex part 38 is pressed, and therefore the pair of pushing parts 139 are spaced from each other in the width direction C and the convex part 38 passes from the upward direction B1 to the downward direction B2 between the pairs of pushing parts 139 in the through hole 135 (a slit). That is, the gap between the pair of pushing parts 139 in the width direction C is expanded in a right direction C1 and a left direction C2 of the width direction C by the convex part 38 and the convex part 38 passes in the downward direction B2 while the gap between the pair of pushing parts 139 is expanded.

After the convex part 38 passes between the pair of pushing parts 139, the pair of pushing parts 139 return to their original positions due to the elasticity of the material. That is, in the width direction C, the pair of pushing parts 139 approach each other and return to the position shown in FIG. 23.

Figure 26C:
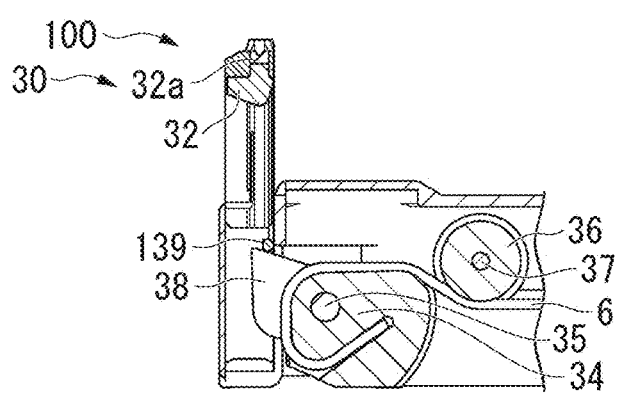
FIG. 26C is a cross-sectional view showing an operation following that of FIG. 26B in the reloading step of the medical stapler.
Figure 26C:
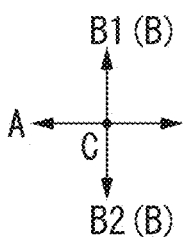

FIG. 26C is a cross-sectional view showing the operation following that of FIG. 26B in the reloading step S20 of the medical stapler 100. After the convex part 38 passes between the pairs of pushing parts 139, the cartridge 30 is located in the upward direction B1 of the convex part 38, as shown in FIG. 26C.

As shown in FIGS. 26B and 26C, the pushing part 139 moves from the downward direction B2 to the upward direction B1 of the convex part 38 when the convex part 38 passes through the through hole 135.

Figure 26D:
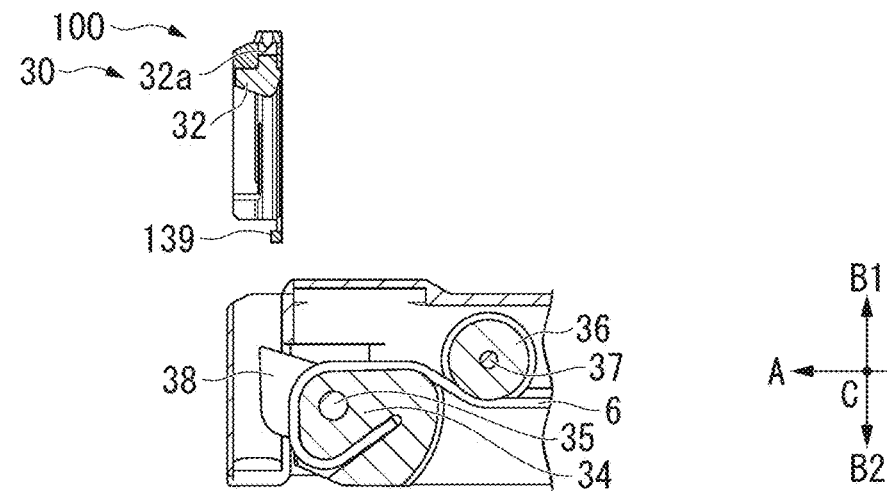
FIG. 26D is a cross-sectional view showing an operation following that of FIG. 26C in the reloading step of the medical stapler.

FIG. 26D is a cross-sectional view showing the operation following that of FIG. 26C in the reloading step S20 of the medical stapler 100. As shown in FIG. 26D, the practitioner can pull the cartridge 30 from the first grasping member 21 in the upward direction B1 and remove the cartridge 30 from the staple release part 3.

Next, an operation of removing the cartridge 30 from the staple release part 3 and then reloading the cartridge 30 into the staple release part 3 will be described with reference to FIGS. 27A to 27C.

Figure 27A:
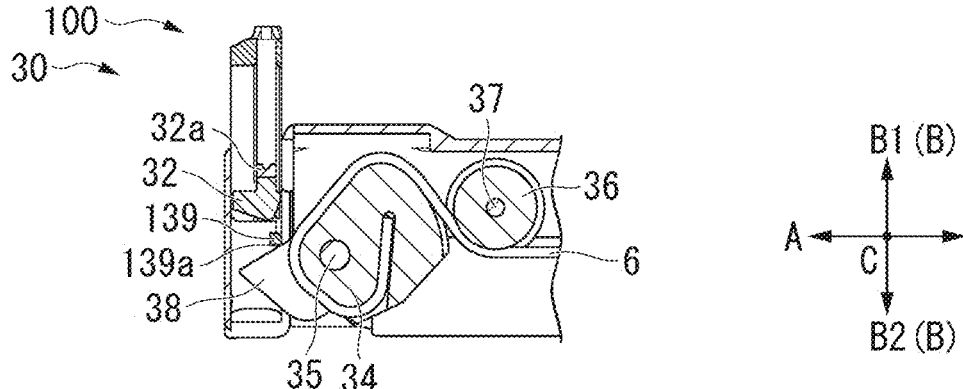
FIG. 27A is a cross-sectional view showing an operation following that of FIG. 26D in the reloading step of the medical stapler.

FIG. 27A is a cross-sectional view showing the operation following that of FIG. 26D in the reloading step S20 of the medical stapler. The operation shown in FIG. 27A is an operation of reloading the cartridge 30 into the staple release part 3 in a state in which the cartridge 30 is removed.

Figure 27B:
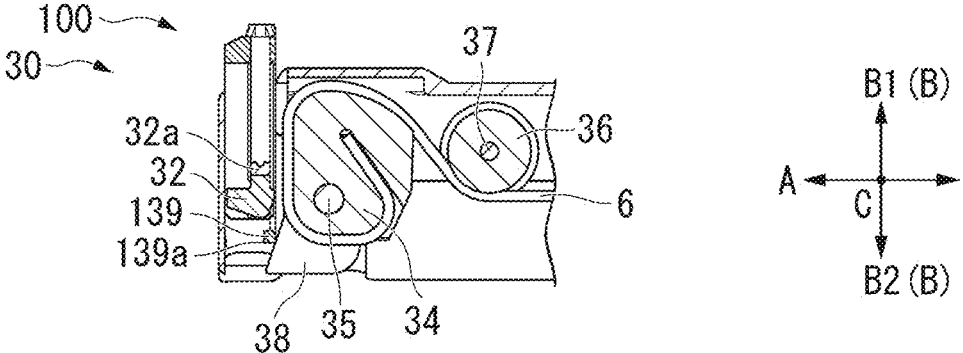
FIG. 27B is a cross-sectional view showing an operation following that of FIG. 27A in the reloading step of the medical stapler.
Figure 27C:
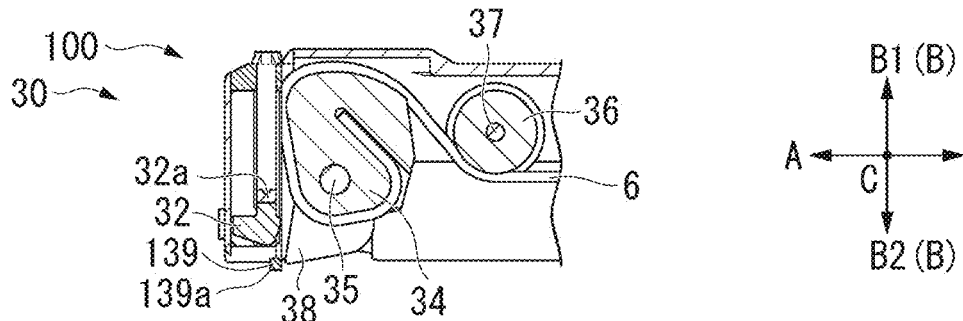
FIG. 27C is a cross-sectional view showing an operation following that of FIG. 27B in the reloading step of the medical stapler.

Here, the cartridge 30 that is reloaded accommodates the staples S, but the staples S are omitted in the cross-sectional views shown in FIGS. 27A to 27C. The cartridge 30 to be reloaded may be, for example, the cartridge 30 removed in FIGS. 26A to 26D in which the practitioner contains the staples S, or a separate cartridge 30 other than the removed cartridge 30.

As shown in FIG. 27A, the practitioner inserts the cartridge 30 that is reloaded into the concave part 21g of the first grasping member 21 from the upward direction B1. In this case, because the staples S are accommodated in the staple storage part 31 of the cartridge 30, the straight-moving member 32 is moved in the downward direction B2 with respect to the staple storage part 31.

When the cartridge 30 is reloaded, the lower surface 139a of the pushing part 139 of the second member 132 is in contact with the convex part 38 from the upward direction B1 as shown in FIG. 27A. Therefore, when the cartridge 30 is moved in the downward direction B2 with respect to the first grasping member 21, the convex part 38 is pushed by the pushing part 139 in the downward direction B2 and the first pulley 34 rotates. At this time, the practitioner does not manipulate the release manipulation wire 6.

FIG. 27B is a cross-sectional view showing the operation following that of FIG. 27A in the reloading step S20 of the medical stapler. As shown in FIG. 27B, when the cartridge 30 is further moved in the downward direction B2 from the state shown in FIG. 27A, the convex part 38 of the first pulley 34 is pushed by the pushing part 139 and further rotated to move in the downward direction B2.

FIG. 27C is a cross-sectional view showing the operation following that of FIG. 27B in the reloading step S20 of the medical stapler. As shown in FIG. 27C, when the cartridge 30 is further moved from the state shown in FIG. 27B in the downward direction B2, the convex part 38 of the first pulley 34 is pushed by the pushing part 139 and further rotated to move to the proximal end side of the pushing part 139.

Because the convex part 38 is located on the proximal end side of the pushing part 139, the pushing part 139 can move in the downward direction B2 of the convex part 38. Therefore, the cartridge 30 can be sufficiently inserted into the first grasping member 21 and the cartridge 30 can be attached to the staple release part 3. In this case, the convex part 38 and the straight-moving member 32 are not in contact with each other.

In addition, when the cartridge 30 is fixed to the staple release part 3 via the connection member 39, the connection member 39 is inserted into the insertion hole 137 of the first member 131 and the insertion hole 138 of the second member 132 and the cartridge 30 is fixed to the staple release part 3 in the state shown in FIG. 27C.

Here, the position of the first pulley 34 (the rotation member 33) shown in FIG. 27C is referred to as a "first position." The first position is the initial position of the rotation member 33. That is, in the reloading step S20, the practitioner can return the rotation member 33 to the initial position by attaching the cartridge 30 to the staple release part 3.

After reloading the cartridge 30 containing the staples S in the reloading step S20 into the staple release part 3, the practitioner returns to the insertion step S12 and performs subsequent steps again. For example, when all the suturing of the treatment target T has not been completed in the first suturing step S17, the practitioner performs the suturing treatment again using the staples S accommodated in the cartridge 30 reloaded in the reloading step S20.

When the steps are performed from the insertion step S12 again after the reloading step S20, the practitioner manipulates the release manipulation wire 6 to rotate the rotation member 33 in the suturing step S17.

At this time, because the rotation member 33 is located at the first position by the reloading step S20, the practitioner pulls the release manipulation wire 6 and causes the convex part 38 and the straight-moving member 32 to be in contact with each other, resulting in the state of FIG. 12.

The practitioner further pulls the release manipulation wire 6 to eject the staple S from the staple release part 3 and perform the suturing treatment again. In this case, as described above, the rotation member 33 is rotated to the position shown in FIG. 26A. Here, the position of the rotation member 33 shown in FIG. 26A is referred to as a "second position." That is, in the rotation member 33, the second position is a position when the staple S is ejected from the staple release part 3.

The rotation member 33 can be rotated from the first position, which is the initial position, to the second position where the staple S is ejected by the pulling manipulation of the release manipulation wire 6. Moreover, in the reloading step S20, the rotation member 33 is located at the second position when the cartridge 30 is removed from the staple release part 3. Moreover, when the cartridge 30 is attached to the staple release part 3, the rotation member 33 rotates from the second position to the first position and returns to the initial position.

Moreover, in the reloading step S20, the pushing part 139 of the cartridge 30 moves from the downward direction B2 to the upward direction B1 of the rotation member 33 located at the second position when the cartridge 30 is removed from the staple release part 3. Moreover, when the cartridge 30 is attached to the staple release part 3, the pushing part 139 pushes the rotation member 33 located at the second position from the upward direction B1 to the downward direction B2 and therefore the rotation member 33 rotates to the first position and returns to the initial position.

Thus, after the suturing step S17, the practitioner can remove the cartridge 30 from the staple release part 3 and attach the cartridge 30 containing the staples S to the staple release part 3, thereby reloading the staples S into the medical stapler 100 and continuing the suturing treatment. Moreover, because the rotation member 33 returns to the initial position (the first position) according to an operation of attaching the cartridge 30 to the staple release part 3, the practitioner (the manipulator) can easily return the rotation member 33 to the initial position and easily recognizes that the rotation member has returned to the initial position.

After completing all suturing treatments, the practitioner removes the medical stapler 100 from the body in the removal step S18 and ends the manipulation (step S21).

When the suturing treatment is performed a plurality of times by performing the reloading step S20, it may be difficult to visually recognize the staple S used by the practitioner for suturing at a part that has already been sutured. Therefore, it is preferable to provide a marking member for improving visibility in the staple S used in the medical stapler 100.

Figure 28:
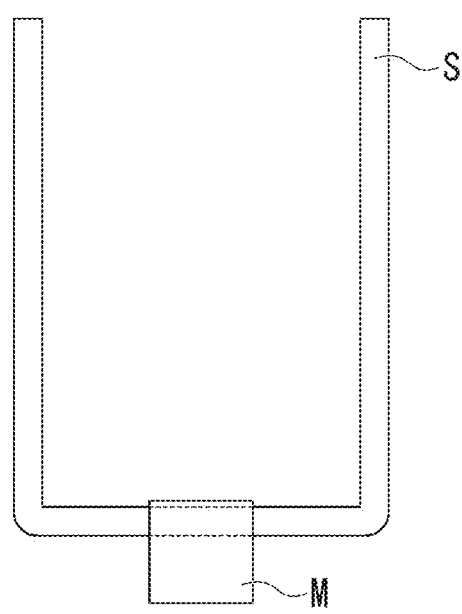
FIG. 28 is a front view showing a staple having a marking member.

FIG. 28 is a front view showing the staple S having the marking member M. The marking member M is connected in the downward direction B2 of the staple S in the staple S accommodated in the medical stapler 100. Therefore, even for the staple S ejected from the staple release part 3 in the suturing step S17 and in a state in which the needle tip S1 has penetrated through the treatment target T, the practitioner can visually recognize the marking member M via the imaging unit of the endoscope 200.

The marking member M is made of a material that can be highlighted by image enhancement light such as, for example, narrow band imaging (NBI) or autofluorescence imaging (AFI). Here, NBI is a technique (method) for highlighting capillaries and mucosal fine patterns in the mucosal surface layer by applying light of two narrowed wavelengths easily absorbed by hemoglobin in the blood. In NBI, in order to observe blood vessels with high contrast, attention is paid to the use of light having both a feature of strong absorption by blood and a feature of strong reflection and scattering in a mucosal surface layer, blue narrowband light (390 to 445 nm) is used for capillary observation of the mucosal surface layer, and green narrow-band light (530 to 550 nm) is used to highlight the contrast between the observation of deep thick blood vessels and the capillaries of the mucosal surface.

For example, when light hits a solid substance, light of a wavelength specific to the solid substance is absorbed. Moreover, light with a wavelength that is not absorbed by the solid substances is reflected. Because the human eye receives light of a wavelength that has not been absorbed by the substance, the color of the wavelength of the reflected light is determined to be the color of the substance. Therefore, the color of the solid substance is the complementary color of the color of light absorbed by the solid substance.

Therefore, the marking member M can be highlighted by setting the color of the marking member M to a color in which it is difficult to absorb the above-described NBI light. Specifically, the marking member M can be highlighted by adopting violet or green. Moreover, it is possible to highlight the staple S as well as the marking member M by setting the color of the staple S to violet or green.

The means for highlighting the staple S and the marking member M is not limited to a method using NBI, and, for example, a fluorescent substance such as indocyanine green (ICG), whose fluorescence is excited when near-infrared light is applied, may be adopted in the staple S or the marking member M and highlighted.

It is only necessary for the dimensions of the marking member M to be dimensions that can be visually recognized by the practitioner via the imaging unit of the endoscope 200. For example, when the marking member M is formed of a material that can be highlighted by image enhancement light, the marking member M may be a member with a small dimension with respect to the staple S. Even if the marking member M is small, visibility can be improved by highlighting the marking member M with image enhancement light. In addition, the marking member M is preferably formed of a biocompatible material.

Moreover, the visibility of the staple S can be improved by increasing the dimensions of a portion where the marking member M projects from the staple S. Therefore, in the marking member M, the dimension of the portion projecting from the staple S is preferably larger than the wire diameter of the staple S.

Moreover, when the staple S to which the marking member M is fixed is accommodated in the cartridge 30, the cartridge 30 preferably has a space (a relief part) in which the marking member M fits. For example, by making the shape of the concave part 32a of the straight-moving member 32 into a shape in which the marking member M fits, the cartridge 30 can have a relief part in which the marking member M fits. The marking member M preferably has a dimension (width) that fits into the relief part of the cartridge 30.

As described above, the visibility of the staple S can be improved by having the marking member M. It is only necessary for the marking member M to improve the visibility of the staple S. A resin member, a metallic member, a tape-like member, a thread-like member, and the like can be adopted as the marking member M.

The medical stapler 100 of the present embodiment includes the staple release part 3 having the rotation member 33 (an injection mechanism) capable of rotating (moving) between a first position, which is an initial position, and a second position where the staple S is ejected by the pulling manipulation of the release manipulation wire 6 and the cartridge 30 removably provided on the staple release part 3.

Moreover, the rotation member 33 is located at the second position when the cartridge 30 is removed from the staple release part 3 and rotates from the second position to the first position when the cartridge 30 is attached to the staple release part 3.

As a result, in the medical stapler 100 (a suturing mechanism), the rotation member 33 can easily return to the initial position (the first position). The medical stapler 100 for allowing the manipulator (the practitioner) to easily recognize that the rotation member 33 has returned to the initial position can be provided.

Moreover, because the rotation member 33 returns to the initial position in conjunction with an operation of attaching the cartridge 30 to the staple release part 3, it is possible to suppress forgetting to return to the initial position.

Although the embodiment of the present invention has been described above in detail with reference to the drawings, the specific configuration is not limited to this embodiment and also includes design changes and the like without departing from the spirit and scope of the present invention. Moreover, constituent elements shown in the above-described embodiment and modified examples to be described below can be appropriately combined and configured.

Modified Example 1

Although the cartridge 30 rotates the rotation member 33 to the first position by performing a pushing operation of the pushing part 139 in the above-described embodiment, an aspect of the cartridge is not limited thereto.

The cartridge may push the rotation member 33 in the downward direction B2 with the straight-moving member 32, and rotate the rotation member 33 to the first position. In this case, the cartridge may not have the pushing part 139.

Moreover, when the rotation member 33 is pushed by the straight-moving member 32, there is a possibility that the straight-moving member 32 will move in the upward direction B1 by the rotation member 33. When the rotation member 33 is pushed by the straight-moving member 32, for example, a cover member that regulates the movement of the straight-moving member 32 in the upward direction B1 is inserted into the staple storage part 31 from the upward direction B1, such that it is possible to suppress the movement of the straight-moving member 32 in the upward direction B1 by the rotation member 33.

In this case, when the cartridge is attached to the staple release part 3, the cover member is inserted into the staple storage part 31 of the cartridge from the upward direction B1 and fixed. After the cartridge is attached to the staple release part 3 in a state in which the movement of the straight-moving member 32 is regulated in the upward direction B1 with the cover member, the practitioner removes the cover member from the cartridge. The cover member is removed, such that the straight-moving member 32 can move in the upward direction B1 and the staple S can be ejected.

Modified Example 2

Although the staple S has sufficient visibility by providing the marking member M in the above-described embodiment, an aspect of the staple is not limited thereto.

The visibility of the staple may be improved by coating a surface of the staple with a material that can be highlighted by image enhancement light. Moreover, the visibility of the staple may be improved by forming the staple with a material that can be highlighted by image enhancement light.

Modified Example 3

Although the concave part 32a of the cartridge 30 is fitted with the staple S stored in the staple storage part 31 and separated from the staple S when the staple S is ejected in the above-described embodiment, an aspect of the concave part is not limited thereto.

The concave part contained in the cartridge may be ejected from the staple release part 3 together with the staple S in a state in which a connection to the staple S is made when the staple S is fitted and the staple S is ejected. In the suturing treatment, the staple S and the concave part are ejected in a state in which they are connected, and the visibility of the staple S can be improved by the concave part by suturing the treatment target T. At this time, the concave part may be connected (coupled) with the staple S when the staple S ejected from the staple release part 3 is pressed against the pocket 41 of the staple accommodation part 4 and deformed.

Moreover, a diameter of a groove shape (a groove part) of the concave part is preferably slightly smaller than a diameter of the staple S. Here, the groove shape of the concave part is a portion that is concave in the downward direction B2 and supports the staple S from the downward direction B2. In addition, it is not limited to the overall diameter in the groove shape of the concave part and it is only necessary for the diameter of a part of the groove shape of the concave part to be slightly smaller than the diameter of the staple S. Moreover, a claw shape (a claw part) may be provided at an opening (an inlet) of the groove shape of the concave part in the upward direction B1 and the staple S and the concave part may be connected by this claw shape.

What is claimed is:

1. A medical stapler provided at a distal end of an endoscope, the medical stapler comprising:
   a first grasping member;
   a second grasping member connected to the first grasping member so that the first grasping member and the second grasping member are configured to be opened and closed;
   a wire extending in an axial direction of the endoscope; and
   a staple release part having a cartridge configured to accommodate a staple and an injection mechanism connected to a distal end of the wire and configured to eject the staple from the cartridge, wherein:
      the cartridge is provided so that the cartridge is removably attached to the staple release part;
      the injection mechanism includes a rotation member configured to rotate about a rotation shaft;
      the rotation member is movable from a first position that is an initial position to a second position where the staple is ejected by manipulating the wire;
      the injection mechanism is located at the second position when the cartridge is removed from the staple release part;
      the injection mechanism moves from the second position to the first position when the cartridge is attached to the staple release part;
      the staple release part is positioned on a distal end side of the first grasping member relative to the rotation shaft:
      the rotation member has a convex part extending radially from the rotation shaft;
      the staple is configured to be released from the cartridge in a direction from the first grasping member toward the second grasping member;
      the staple release part has a support member configured to move in a direction that the staple is released with respect to the cartridge;

the cartridge has a slit extending in the direction that the staple is released; and
      a part of the convex part is configured to pass through the slit and be in contact with the support member when the rotation member moves between the first position and the second position with respect to the cartridge.

2. The medical stapler according to claim 1, wherein:
   the support member is movable in a vertical direction by supporting the staple from a downward direction; and
   when the wire is pulled:
      the injection mechanism moves the support member from the downward direction to an upward direction while moving from the first position to the second position; and
      the staple is ejected from the staple release part in the upward direction by the support member.

3. The medical stapler according to claim 2, wherein:
   the cartridge includes a pushing part located in the downward direction of the support member;
   the pushing part moves from the downward direction to the upward direction of the injection mechanism located at the second position when the cartridge is removed from the staple release part; and
   the injection mechanism located at the second position is pushed from the upward direction to the downward direction and moved to the first position when the cartridge is attached to the staple release part.

4. The medical stapler according to claim 3, wherein the pushing part includes the slit open in the downward direction, and wherein the pushing part moves from the downward direction to the upward direction of the injection mechanism by allowing the injection mechanism to pass through the slit when the cartridge is removed from the staple release part.

5. The medical stapler according to claim 1, wherein the cartridge is attached to the staple release part in a state in which the staple is accommodated.

6. The medical stapler according to claim 1, wherein the injection mechanism is rotatable between the first position and the second position.

7. The medical stapler according to claim 1, wherein the cartridge is configured to accommodate the staple being substantially U-shaped and having an opening in an upward direction, and wherein a marking member including a material highlighted by image enhancement light is connected to the staple in a downward direction.

8. The medical stapler according to claim 7, wherein the staple includes a material highlighted by image enhancement light.

9. The medical stapler according to claim 7, wherein the marking member has a dimension of a part projecting from the staple larger than a wire diameter of the staple.

10. The medical stapler according to claim 7, wherein the support member is configured to support the staple from a downward direction, the support member being movable in a vertical direction, and wherein the support member has a relief part configured to accommodate the marking member.

11. The medical stapler according to claim 10, wherein the marking member has a dimension in which the marking member is configured to be accommodated in the relief part.

12. The medical stapler according to claim 7, wherein the marking member is fixed to the staple.

13. The medical stapler according to claim 2, wherein, when the injection mechanism has moved from the first position to the second position, the support member is connected to the staple and ejected from the staple release part together with the staple in the upward direction.

14. The medical stapler according to claim 13, wherein the support member has a concave part having a groove shape concave in the downward direction, the concave part being configured to support the staple from the downward direction, and wherein a diameter of the groove shape in the concave part is slightly smaller than a diameter of the staple.

15. The medical stapler according to claim 13, wherein the support member has a concave part having a groove shape concave in the downward direction, the concave part being configured to support the staple from the downward direction, and wherein the concave part has at least a part of an opening in the upward direction in the groove shape, the part of the opening being smaller than a diameter of the staple.

\* \* \* \* \*